(12) United States Patent
Neumann

(10) Patent No.: US 11,984,199 B2
(45) Date of Patent: May 14, 2024

(54) METHODS AND SYSTEMS FOR GENERATING COMPATIBLE SUBSTANCE INSTRUCTION SETS USING ARTIFICIAL INTELLIGENCE

(71) Applicant: Kenneth Neumann, Lakewood, CO (US)

(72) Inventor: Kenneth Neumann, Lakewood, CO (US)

(73) Assignee: KPN INNOVATIONS, LLC, Lakewood, CO (US)

(*) Notice: Subject to any disclaimer, the term of this patent is extended or adjusted under 35 U.S.C. 154(b) by 1321 days.

(21) Appl. No.: 16/530,329

(22) Filed: Aug. 2, 2019

(65) Prior Publication Data
US 2021/0035658 A1 Feb. 4, 2021

(51) Int. Cl.
*G16B 40/20* (2019.01)
*G06N 20/00* (2019.01)
(Continued)

(52) U.S. Cl.
CPC .............. *G16B 40/20* (2019.02); *G06N 20/00* (2019.01); *G16B 40/30* (2019.02); *G16C 20/70* (2019.02); *G16H 20/60* (2018.01)

(58) Field of Classification Search
CPC ................................................ G06Q 50/20–26
See application file for complete search history.

(56) References Cited

U.S. PATENT DOCUMENTS

| | | | | |
|---|---|---|---|---|
| 5,750,994 A | * | 5/1998 | Schlager | A61B 5/1495 250/339.11 |
| 5,769,074 A | * | 6/1998 | Barnhill | G01N 33/573 600/300 |

(Continued)

FOREIGN PATENT DOCUMENTS

| | | |
|---|---|---|
| CN | 103984847 A | 8/2014 |
| RU | 2689423 C1 | 5/2019 |
| WO | 2018031991 | 2/2018 |

OTHER PUBLICATIONS

Genopalate; Our Science; Jul. 10, 2019.
(Continued)

*Primary Examiner* — Neal Sereboff
(74) *Attorney, Agent, or Firm* — Caldwell Intellectual Property Law

(57) ABSTRACT

A system for generating a compatible substance instruction set using artificial intelligence. The system includes at least a server, wherein the at least a server is configured to receive at least a biomarker datum from a user client device. The at least a server is configured to categorize the at least a biomarker datum as a function of a biomarker system classification to produce at least a classified biomarker datum. The at least a server is configured to receive training data and to retrieve training data from a database. The at least a server is configured to select at least a first machine-learning model as a function of the first training set and the at least a classified biomarker datum. The at least a server is configured to generate at least a compatible substance instruction set containing at least a recommended compatible substance as a function of the at least a classified biomarker datum, the first training set, and the at least a first machine-learning model.

18 Claims, 14 Drawing Sheets

(51) Int. Cl.
    *G16B 40/30*     (2019.01)
    *G16C 20/70*     (2019.01)
    *G16H 20/60*     (2018.01)

(56) References Cited

U.S. PATENT DOCUMENTS

| | | |
|---|---|---|
| 8,000,982 B2 | 8/2011 | Kane et al. |
| 8,762,167 B2 | 6/2014 | Blander et al. |
| 2013/0018832 A1* | 1/2013 | Ramanathan ............ G06N 3/08 706/25 |
| 2013/0151270 A1 | 6/2013 | Nova et al. |
| 2014/0088996 A1 | 3/2014 | Damani |
| 2018/0240542 A1 | 8/2018 | Grimmer et al. |
| 2019/0205771 A1* | 7/2019 | Lin ..................... G06F 40/30 |
| 2020/0168305 A1* | 5/2020 | Bashir ................. G06N 20/00 |
| 2020/0320428 A1* | 10/2020 | Chaloulos ............. G06N 20/00 |

OTHER PUBLICATIONS

CMAJ Jan. 9, 2017;189:E40-1. doi: 10.1503/cmaj.109-5352; https://www.ncbi.nlm.nih.gov/pmc/articles/PMC5224962/pdf/1890e40.pdf retrieved on Jul. 10, 2019.

* cited by examiner

Compatible Substance Index Value Database 156

Alfalfa Sprout Table 1004

Hazelnut Table 1008

Green Tea Table 1012

Lamb Table 1016

Munster Cheese Table 1020

Raspberry Table 1024

FIG. 10

METHODS AND SYSTEMS FOR GENERATING COMPATIBLE SUBSTANCE INSTRUCTION SETS USING ARTIFICIAL INTELLIGENCE

FIELD OF THE INVENTION

The present invention generally relates to the field of artificial intelligence. In particular, the present invention is directed to methods and systems for generating compatible substance instruction sets using artificial intelligence.

BACKGROUND

Accurate assessment of compatibility is challenging due to the vast magnitude of factors to be considered and analyzed. Incorrect assessment can prolong illness and detract from achieving a vibrant state. Accurate and informed analysis is of utmost importance when determining compatibility of substances.

SUMMARY OF THE DISCLOSURE

In an aspect, a system for generating a compatible substance instruction set using artificial intelligence. The system includes at least a server wherein the at least a server is designed and configured to receive at least a biomarker datum wherein the at least a biomarker datum contains at least an element of body data correlated to at least a body dimension. The at least a server is designed and configured to categorize the at least a biomarker datum as a function of the at least a body dimension to produce at least a classified biomarker datum. The at least a server is designed and configured to receive training datum, wherein receiving the training data further comprises receiving a first training set including a plurality of first data entries, each first data entry of the plurality of first data entries including at least a first element of first classified biomarker data and at least a correlated compatible substance label. The at least a server is designed and configured to select at least a first machine-learning model as a function of the first training set and the at least a classified biomarker datum. The at least a server is designed and configured to generate at least a first machine-learning model using the first training set wherein the first machine-learning model outputs at least a compatible substance containing at least a compatible substance index value as a function of relating the at least a user biomarker datum to at least a compatible substance using the first training set and the at least a first machine-learning model. The at least a server is designed and configured to generate at least a compatible substance instruction set containing the at least a compatible substance ranked as a function of the at least a compatible substance index value.

In an aspect, a method of generating a compatible substance instruction set using artificial intelligence. The method includes receiving by at least a server at least a biomarker datum wherein the at least a biomarker datum contains at least an element of body data correlated to at least a body dimension. The method includes categorizing by the at least a server the at least a biomarker datum as a function of the at least a body dimension to produce at least a classified biomarker datum. The method includes receiving by the at least a server training datum, wherein receiving the training data further comprises receiving a first training set including a plurality of first data entries, each first data entry of the plurality of first data entries including at least a first element of first classified biomarker data and at least a correlated compatible substance label. The method includes selecting by the at least a server at least a first machine-learning model as a function of the first training set and the at least a classified biomarker datum. The method includes generating by the at least a server at least a first machine-learning model using the first training set wherein the first machine-learning model outputs at least a compatible substance containing at least a compatible substance index value as a function of relating the at least a user biomarker datum to at least a compatible substance using the first training set and the at least a first machine-learning model. The method includes generating by the at least a server at least a compatible substance instruction set containing the at least a compatible substance ranked as a function of the at least a compatible substance index value.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein:

FIG. 10 is a block diagram illustrating an exemplary embodiment of a compatible substance index value database;

The drawings are not necessarily to scale and may be illustrated by phantom lines, diagrammatic representations and fragmentary views. In certain instances, details that are not necessary for an understanding of the embodiments or that render other details difficult to perceive may have been omitted.

DETAILED DESCRIPTION

At a high level, aspects of the present disclosure are directed to systems and methods for generating compatible substance instruction set using artificial intelligence. In an embodiment, at least a biomarker datum is received. In an embodiment, at least a biomarker datum may include a tissue sample or an analysis of a bodily fluid. At least a server categorizes the at least a biomarker datum to produce at least a classified biomarker datum. At least a classified biomarker datum may be classified as a function of a dimension of the human body. At least a server receives training data and selects at least a first machine-learning model as a function of the training data. The at least a server generates at least a compatible substance instruction set containing at least a recommended compatible substance as a function of the at least a classified biomarker datum, the training data and the at least a first machine-learning model.

Figure 1:
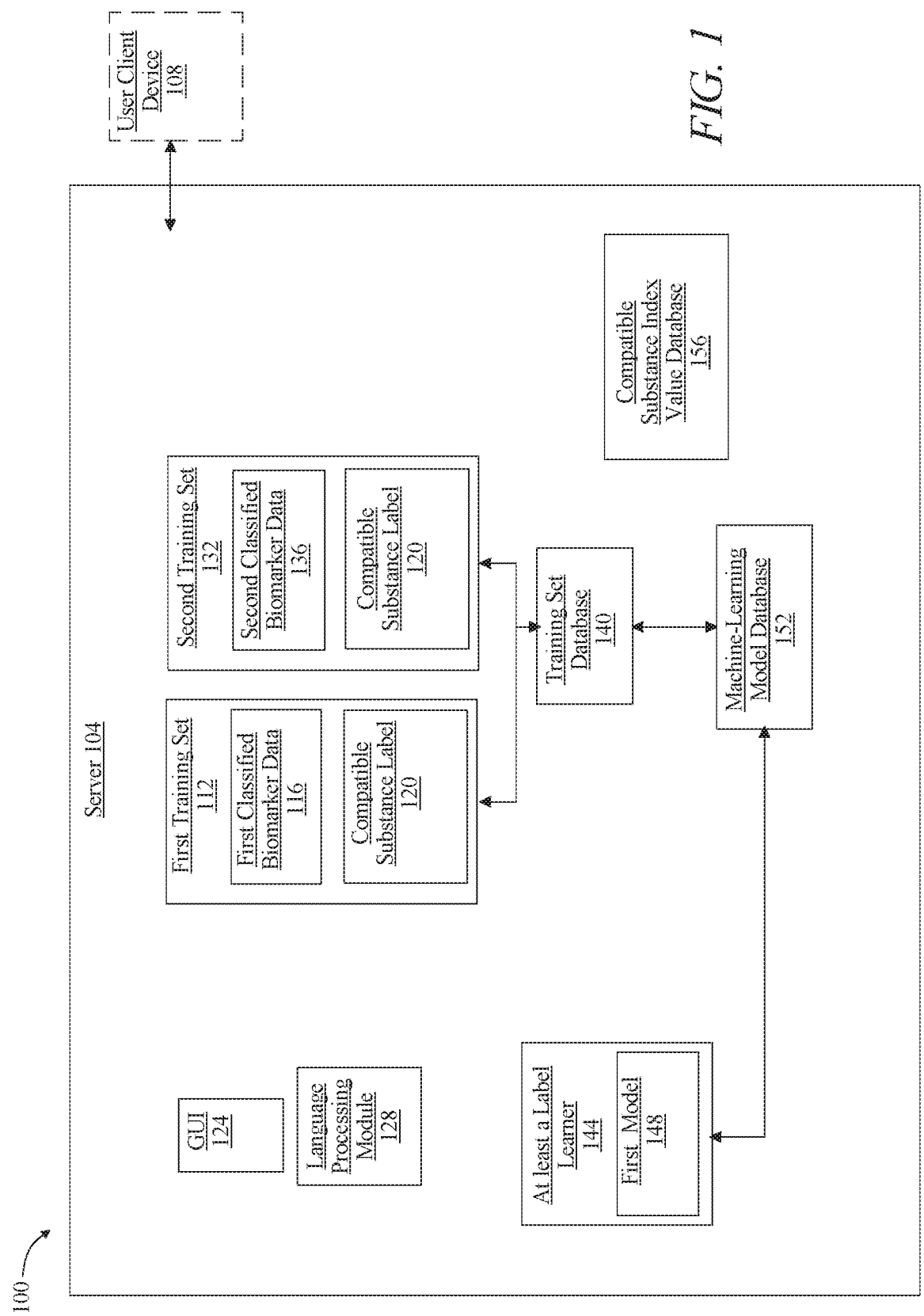
FIG. 1 is a block diagram illustrating an exemplary embodiment of a system for generating a compatible substance instruction set using artificial intelligence.

Turning now to FIG. 1, a system 100 for generating a compatible substance instruction set using artificial intelligence is illustrated. System 100 includes at least a server 104. At least a server 104 may include any computing device as described herein, including without limitation a microcontroller, microprocessor, digital signal processor (DSP) and/or system on a chip (SoC) as described herein. At least a server 104 may be housed with, may be incorporated in, or may incorporate one or more sensors of at least a sensor. Computing device may include, be included in, and/or communicate with a mobile device such as a mobile telephone or smartphone. At least a server 104 may include a single computing device operating independently, or may include two or more computing device operating in concert, in parallel, sequentially or the like; two or more computing devices may be included together in a single computing device or in two or more computing devices. At least a server 104 with one or more additional devices as described below in further detail via a network interface device. Network interface device may be utilized for connecting a at least a server 104 to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network may employ a wired and/or a wireless mode of communication. In general, any network topology may be used. Information (e.g., data, software etc.) may be communicated to and/or from a computer and/or a computing device. At least a server 104 may include but is not limited to, for example, at least a server 104 or cluster of computing devices in a first location and a second computing device or cluster of computing devices in a second location. At least a server 104 may include one or more computing devices dedicated to data storage, security, distribution of traffic for load balancing, and the like. At least a server 104 may distribute one or more computing tasks as described below across a plurality of computing devices of computing device, which may operate in parallel, in series, redundantly, or in any other manner used for distribution of tasks or memory between computing devices. At least a server 104 may be implemented using a "shared nothing" architecture in which data is cached at the worker, in an embodiment, this may enable scalability of system 100 and/or computing device.

With continued reference to FIG. 1, at least a server 104 is configured to receive at least a biomarker datum wherein the at least a biomarker datum contains at least an element of body data correlated to at least a body dimension. Biomarker datum, as used herein includes any element and/or elements of physiological state data. At least a biomarker datum may include a physically extraction sample, where a "physically extracted sample" as used in this disclosure is a sample obtained by removing and analyzing tissue and/or fluid. Physically extracted sample may include without limitation a blood sample, a tissue sample, a buccal swab, a mucous sample, a stool sample, a hair sample, a fingernail sample, or the like. For example and without limitation, at least a biomarker datum may include a hair sample that has been analyzed for specific nutrients or a saliva sample that has been analyzed for specific hormone levels. At least an element of body data may include at least a datum of user test data containing at least a root system label. User test data may include any data describing results obtained from a physically extracted sample from a user. For example, user test data may include results describing a urinalysis of a user examining for the absence or presence of ketones. In yet another non-limiting example, user test data may include results from a user's salivary hormone levels or results from a stool analysis. Root system label may include any label indicating a particular root cause of a user's test result. Root system may be correlated to a body dimension and may include information correlating a test result to a given body dimension. For example, at least an element of user test data showing elevated thyroid stimulating hormone level (TSH) outside normal limits may contain a root system label that indicates Hashimoto's thyroiditis which may be correlated to microbiome body dimension. In yet another non-limiting example, at least an element of user test data showing lactulose accumulated in urine sample after lactulose and mannitol consumption may contain a root system label that indicates leaky gut which may be correlated to gut wall body dimension.

With continued reference to FIG. 1, at least a biomarker datum may be categorized as a function of a biomarker system classification. Biomarker system classification, as used herein, includes categories of biomarker datums having shared characteristics as related to a dimension of the human body. Dimension of the human body includes particular root cause pillars of disease. Dimension of the human body include epigenetics, gut wall, microbiome, nutrients, genetics, and metabolism. Correcting deficiencies found within specific dimensions of the human body may aid a user in achieving vibrant health and longevity. At least an element of data contained within biomarker datum is correlated to at least a body dimension. Correlated may include a shared trait and/or shared data element classified to a particular body dimension. For instance and without limitation, a biomarker datum containing at least an element of microbiome data including for example species of specific strains of bacteria within the gastrointestinal tract may be correlated to a body dimension such as microbiome. In yet another non-limiting example, a biomarker datum containing at least an element of a phenotype of a particular gene may be correlated to a body dimension such as genetics. In an embodiment, at least an element of data may be correlated to a plurality of body dimensions. For instance and without limitation, at least an element of body data such as a stool chemistry analysis may be correlated to a microbiome body dimension and a gut wall body dimension.

With continued reference to FIG. 1, epigenetic, as used herein, includes any biomarker describing changes to a genome that do not involve corresponding changes in nucleotide sequence. Epigenetic biomarker may include data describing any heritable phenotypic. Phenotype, as used herein, include any observable trait of a user including morphology, physical form, and structure. Phenotype may include a user's biochemical and physiological properties, behavior, and products of behavior. Behavioral phenotypes may include cognitive, personality, and behavior patterns. This may include effects on cellular and physiological phenotypic traits that may occur due to external or environmental factors. For example, DNA methylation and histone modification may alter phenotypic expression of genes without altering underlying DNA sequence. Epigenetic biomarkers may include data describing one or more states of methylation of genetic material.

With continued reference to FIG. 1, gut wall, as used herein, includes the space surrounding the lumen of the gastrointestinal tract that is composed of four layers including the mucosa, submucosa, muscular layer, and serosa. The mucosa contains the gut epithelium that is composed of goblet cells that function to secrete mucus, which aids in lubricating the passage of food throughout the digestive tract. The goblet cells also aid in protecting the intestinal wall from destruction by digestive enzymes. The mucosa includes villi or folds of the mucosa located in the small intestine that increase the surface area of the intestine. The villi contain a lacteal, that is a vessel connected to the lymph system that aids in removal of lipids and tissue fluids. Villi may contain microvilli that increase the surface area over which absorption can take place. The large intestine lack villi and instead a flat surface containing goblet cells are present.

With continued reference to FIG. 1, gut wall includes the submucosa, which contains nerves, blood vessels, and elastic fibers containing collagen. Elastic fibers contained within the submucosa aid in stretching the gastrointestinal tract with increased capacity while also maintaining the shape of the intestine. Gut wall includes muscular layer which contains smooth muscle that aids in peristalsis and the movement of digested material out of and along the gut. Gut wall includes the serosa which is composed of connective tissue and coated in mucus to prevent friction damage from the intestine rubbing against other tissue. Mesenteries are also found in the serosa and suspend the intestine in the abdominal cavity to stop it from being disturbed when a person is physically active.

With continued reference to FIG. 1, gut wall biomarker may include data describing one or more test results including results of gut wall function, gut wall integrity, gut wall strength, gut wall absorption, gut wall permeability, intestinal absorption, gut wall barrier function, gut wall absorption of bacteria, gut wall malabsorption, gut wall gastrointestinal imbalances and the like.

With continued reference to FIG. 1, gut wall biomarker may include data describing blood test results of creatinine levels, lactulose levels, zonulin levels, and mannitol levels. Gut wall biomarker may include blood test results of specific gut wall biomarkers including d-lactate, endotoxin lipopolysaccharide (LPS) Gut wall biomarker may include data breath tests measuring lactulose, hydrogen, methane, lactose, and the like. Gut wall biomarker may include blood test results describing blood chemistry levels of albumin, bilirubin, complete blood count, electrolytes, minerals, sodium, potassium, calcium, glucose, blood clotting factors, With continued reference to FIG. 1, gut wall biomarker may include stool test results describing presence or absence of parasites, firmicutes, bacteriodetes, absorption, inflammation, food sensitivities. Stool test results may describe presence, absence, and/or measurement of acetate, aerobic bacterial cultures, anerobic bacterial cultures, fecal short chain fatty acids, beta-glucuronidase, cholesterol, chymotrypsin, fecal color, cryptosporidium EIA, *Entamoeba histolytica*, fecal lactoferrin, *Giardia lamblia* EIA, long chain fatty acids, meat fibers and vegetable fibers, mucus, occult blood, parasite identification, phospholipids, propionate, putrefactive short chain fatty acids, total fecal fat, triglycerides, yeast culture, n-butyrate, pH and the like.

With continued reference to FIG. 1, gut wall biomarker may include stool test results describing presence, absence, and/or measurement of microorganisms including bacteria, archaea, fungi, protozoa, algae, viruses, parasites, worms, and the like. Stool test results may contain species such as *Bifidobacterium* species, *Campylobacter* species, *Clostridium difficile, Cryptosporidium* species, *Cyclospora cayetanensis, Cryptosporidium* EIA, *Dientamoeba fragilis, Entamoeba histolytica, Escherichia coli, Entamoeba histolytica, Giardia, H. pylori, Candida albicans, Lactobacillus* species, worms, macroscopic worms, mycology, protozoa, Shiga toxin *E. coli*, and the like.

With continued reference to FIG. 1, gut wall biomarker may include microscopic ova exam results, microscopic parasite exam results, protozoan polymerase chain reaction test results and the like. Gut wall biomarker may include enzyme-linked immunosorbent assay (ELISA) test results describing immunoglobulin G (Ig G) food antibody results, immunoglobulin E (Ig E) food antibody results, Ig E mold results, IgG spice and herb results. Gut wall biomarker may include measurements of calprotectin, eosinophil protein x (EPX), stool weight, pancreatic elastase, total urine volume, blood creatinine levels, blood lactulose levels, blood mannitol levels.

With continued reference to FIG. 1, gut wall biomarker may include data describing one or more procedures examining gut including for example colonoscopy, endoscopy, large and small molecule challenge and subsequent urinary recovery using large molecules such as lactulose, polyethylene glycol-3350, and small molecules such as mannitol, L-rhamnose, polyethyleneglycol-400. Gut wall biomarker may include data describing one or more images such as x-ray, MRI, CT scan, ultrasound, standard barium follow-through examination, barium enema, barium with contract, MRI fluoroscopy, positron emission tomography 9PET), diffusion-weighted MRI imaging, and the like.

With continued reference to FIG. 1, microbiome, as used herein, includes ecological community of commensal, symbiotic, and pathogenic microorganisms that reside on or within any of a number of human tissues and biofluids. For example, human tissues and biofluids may include the skin, mammary glands, placenta, seminal fluid, uterus, vagina, ovarian follicles, lung, saliva, oral mucosa, conjunctiva, biliary, and gastrointestinal tracts. Microbiome may include for example, bacteria, archaea, protists, fungi, and viruses. Microbiome may include commensal organisms that exist within a human being without causing harm or disease. Microbiome may include organisms that are not harmful but rather harm the human when they produce toxic metabolites such as trimethylamine. Microbiome may include pathogenic organisms that cause host damage through virulence factors such as producing toxic by-products. Microbiome may include populations of microbes such as bacteria and yeasts that may inhabit the skin and mucosal surfaces in various parts of the body. Bacteria may include for example *Firmicutes* species, *Bacteroidetes* species, *Proteobacteria* species, *Verrumicrobia* species, *Actinobacteria* species,

*Fusobacteria* species, *Cyanobacteria* species and the like. Archaea may include methanogens such as *Methanobrevibacter smithii* and Methanosphaera stadtmanae. Fungi may include *Candida* species and *Malassezia* species. Viruses may include bacteriophages. Microbiome species may vary in different locations throughout the body. For example, the genitourinary system may contain a high prevalence of *Lactobacillus* species while the gastrointestinal tract may contain a high prevalence of *Bifidobacterium* species while the lung may contain a high prevalence of *Streptococcus* and *Staphylococcus* species.

Microbiome biomarker may include stool test results describing presence, absence, and/or measurement of microorganisms including bacteria, archaea, fungi, protozoa, algae, viruses, parasites, worms, and the like. Stool test results may contain species such as *Akkermansia muciniphila*, *Anaerotruncus colihominis*, bacteriology, *Bacteroides vulgatus*, *Bacteroides-Prevotella*, *Barnesiella* species, *Bifidobacterium longum*, *Bifidobacterium* species, *Butyrivbrio crossotus*, *Clostridium* species, *Collinsella aerofaciens*, fecal color, fecal consistency, *Coprococcus eutactus*, *Desulfovibrio piger*, *Escherichia coli*, *Faecalibacterium prausnitzii*, Fecal occult blood, *Firmicutes* to *Bacteroidetes* ratio, *Fusobacterium* species, *Lactobacillus* species, *Methanobrevibacter smithii*, yeast minimum inhibitory concentration, bacteria minimum inhibitory concentration, yeast mycology, fungi mycology, *Odoribacter* species, *Oxalobacter formigenes*, parasitology, *Prevotella* species, *Pseudoflavonifractor* species, *Roseburia* species, *Ruminococcus* species, *Veillonella* species and the like.

With continued reference to FIG. 1, microbiome biomarker may include stool tests results that identify all microorganisms living a user's gut including bacteria, viruses, archaea, yeast, fungi, parasites, and bacteriophages. Microbiome biomarker may include DNA and RNA sequences from live microorganisms that may impact a user's health. Microbiome biomarker may include high resolution of both species and strains of all microorganisms. Microbiome biomarker may include data describing current microbe activity. Microbiome biomarker may include expression of levels of active microbial gene functions. Microbiome biomarker may include descriptions of sources of disease causing microorganisms, such as viruses found in the gastrointestinal tract such as raspberry bushy swarf virus from consuming contaminated raspberries or Pepino mosaic virus from consuming contaminated tomatoes.

With continued reference to FIG. 1, microbiome biomarker may include blood test results that identify metabolites produced by microorganisms. Metabolites may include for example, indole-3-propionic acid, indole-3-lactic acid, indole-3-acetic acid, tryptophan, serotonin, kynurenine, total indoxyl sulfate, tyrosine, xanthine, 3-methylxanthine, uric acid, and the like.

With continued reference to FIG. 1, microbiome biomarker may include breath test results that identify certain strains of microorganisms that may be present in certain areas of a user's body. This may include for example, lactose intolerance breath tests, methane based breath tests, hydrogen based breath tests, fructose based breath tests. *Helicobacter pylori* breath test, fructose intolerance breath test, bacterial overgrowth syndrome breath tests and the like.

With continued reference to FIG. 1, microbiome biomarker may include urinary analysis for certain microbial strains present in urine. This may include for example, urinalysis that examines urine specific gravity, urine cytology, urine sodium, urine culture, urinary calcium, urinary hematuria, urinary glucose levels, urinary acidity, urinary protein, urinary nitrites, bilirubin, red blood cell urinalysis, and the like.

With continued reference to FIG. 1, nutrient as used herein, includes any substance required by the human body to function. Nutrients may include carbohydrates, protein, lipids, vitamins, minerals, antioxidants, fatty acids, amino acids, and the like. Nutrients may include for example vitamins such as thiamine, riboflavin, niacin, pantothenic acid, pyridoxine, biotin, folate, cobalamin, Vitamin C, Vitamin A, Vitamin D, Vitamin E, and Vitamin K. Nutrients may include for example minerals such as sodium, chloride, potassium, calcium, phosphorous, magnesium, sulfur, iron, zinc, iodine, selenium, copper, manganese, fluoride, chromium, molybdenum, nickel, aluminum, silicon, vanadium, arsenic, and boron.

With continued reference to FIG. 1, nutrients may include extracellular nutrients that are free floating in blood and exist outside of cells. Extracellular nutrients may be located in serum. Nutrients may include intracellular nutrients which may be absorbed by cells including white blood cells and red blood cells.

With continued reference to FIG. 1, nutrient biomarker may include blood test results that identify extracellular and intracellular levels of nutrients. Nutrient biomarker may include blood test results that identify serum, white blood cell, and red blood cell levels of nutrients. For example, nutrient biomarker may include serum, white blood cell, and red blood cell levels of micronutrients such as Vitamin A, Vitamin B1, Vitamin B2, Vitamin B3, Vitamin B6, Vitamin B12, Vitamin B5, Vitamin C, Vitamin D, Vitamin E, Vitamin K1, Vitamin K2, and folate.

With continued reference to FIG. 1, nutrient biomarker may include blood test results that identify serum, white blood cell and red blood cell levels of nutrients such as calcium, manganese, zinc, copper, chromium, iron, magnesium, copper to zinc ratio, choline, inositol, carnitine, methylmalonic acid (MMA), sodium, potassium, asparagine, glutamine, serine, coenzyme q10, cysteine, alpha lipoic acid, glutathione, selenium, eicosapentaenoic acid (EPA), docosahexaenoic acid (DHA), docosapentaenoic acid (DPA), total omega-3, lauric acid, arachidonic acid, oleic acid, total omega 6, and omega 3 index.

With continued reference to FIG. 1, nutrient biomarker may include salivary test results that identify levels of nutrients including any of the nutrients as described herein. Nutrient biomarker may include hair analysis of levels of nutrients including any of the nutrients as described herein.

With continued reference to FIG. 1, genetic as used herein, includes any inherited trait. Inherited traits may include genetic material contained with DNA including for example, nucleotides. Nucleotides include adenine (A), cytosine (C), guanine (G), and thymine (T). Genetic information may be contained within the specific sequence of an individual's nucleotides and sequence throughout a gene or DNA chain. Genetics may include how a particular genetic sequence may contribute to a tendency to develop a certain disease such as cancer or Alzheimer's disease.

With continued reference to FIG. 1, genetic biomarker may include blood tests, hair tests, skin tests, urine, amniotic fluid, buccal swabs and/or tissue test to identify a user's particular sequence of nucleotides, genes, chromosomes, and/or proteins. Genetic biomarker may include tests that example genetic changes that may lead to genetic disorders. Genetic biomarker may detect genetic changes such as deletion of genetic material or pieces of chromosomes that may cause Duchenne Muscular Dystrophy. Genetic biomarker may detect genetic changes such as insertion of genetic material into DNA or a gene such as the BRCA1 gene that is associated with an increased risk of breast and ovarian cancer due to insertion of 2 extra nucleotides. Genetic biomarker may include a genetic change such as a genetic substitution from a piece of genetic material that replaces another as seen with sickle cell anemia where one nucleotide is substituted for another. Genetic biomarker may detect a genetic change such as a duplication when extra genetic material is duplicated one or more times within a person's genome such as with Charcot-Marie Tooth disease type 1. Genetic biomarker may include a genetic change such as an amplification when there is more than a normal number of copies of a gene in a cell such as HER2 amplification in cancer cells. Genetic biomarker may include a genetic change such as a chromosomal translocation when pieces of chromosomes break off and reattach to another chromosome such as with the BCR-ABL1 gene sequence that is formed when pieces of chromosome 9 and chromosome 22 break off and switch places. Genetic biomarker may include a genetic change such as an inversion when one chromosome experiences two breaks and the middle piece is flipped or inverted before reattaching. Genetic biomarker may include a repeat such as when regions of DNA contain a sequence of nucleotides that repeat a number of times such as for example in Huntington's disease or Fragile X syndrome. Genetic biomarker may include a genetic change such as a trisomy when there are three chromosomes instead of the usual pair as seen with Down syndrome with a trisomy of chromosome 21, Edwards syndrome with a trisomy at chromosome 18 or Patau syndrome with a trisomy at chromosome 13. Genetic biomarker may include a genetic change such as monosomy such as when there is an absence of a chromosome instead of a pair, such as in Turner syndrome.

With continued reference to FIG. 1, genetic biomarker may include an analysis of COMT gene that is responsible for producing enzymes that metabolize neurotransmitters. Genetic biomarker may include an analysis of DRD2 gene that produces dopamine receptors in the brain. Genetic biomarker may include an analysis of ADRA2B gene that produces receptors for noradrenaline. Genetic biomarker may include an analysis of 5-HTTLPR gene that produces receptors for serotonin. Genetic biomarker may include an analysis of BDNF gene that produces brain derived neurotrophic factor. Genetic biomarker may include an analysis of 9p21 gene that is associated with cardiovascular disease risk. Genetic biomarker may include an analysis of APOE gene that is involved in the transportation of blood lipids such as cholesterol. Genetic biomarker may include an analysis of NOS3 gene that is involved in producing enzymes involved in regulating vaso-dilation and vaso-constriction of blood vessels.

With continued reference to FIG. 1, genetic biomarker may include ACE gene that is involved in producing enzymes that regulate blood pressure. Genetic biomarker may include SLCO1B1 gene that directs pharmaceutical compounds such as statins into cells. Genetic biomarker may include FUT2 gene that produces enzymes that aid in absorption of Vitamin B12 from digestive tract. Genetic biomarker may include MTHFR gene that is responsible for producing enzymes that aid in metabolism and utilization of Vitamin B9 or folate. Genetic biomarker may include SHMT1 gene that aids in production and utilization of Vitamin B9 or folate. Genetic biomarker may include MTRR gene that produces enzymes that aid in metabolism and utilization of Vitamin B12. Genetic biomarker may include MTR gene that produces enzymes that aid in metabolism and utilization of Vitamin B12. Genetic biomarker may include FTO gene that aids in feelings of satiety or fulness after eating. Genetic biomarker may include MC4R gene that aids in producing hunger cues and hunger triggers. Genetic biomarker may include APOA2 gene that directs body to produce ApoA2 thereby affecting absorption of saturated fats. Genetic biomarker may include UCP1 gene that aids in controlling metabolic rate and thermoregulation of body. Genetic biomarker may include TCF7L2 gene that regulates insulin secretion. Genetic biomarker may include AMY1 gene that aids in digestion of starchy foods. Genetic biomarker may include MCM6 gene that controls production of lactase enzyme that aids in digesting lactose found in dairy products. Genetic biomarker may include BCMO1 gene that aids in producing enzymes that aid in metabolism and activation of Vitamin A. Genetic biomarker may include SLC23A1 gene that produce and transport Vitamin C. Genetic biomarker may include CYP2R1 gene that produce enzymes involved in production and activation of Vitamin D. Genetic biomarker may include GC gene that produce and transport Vitamin D. Genetic biomarker may include CYP1A2 gene that aid in metabolism and elimination of caffeine. Genetic biomarker may include CYP17A1 gene that produce enzymes that convert progesterone into androgens such as androstenedione, androstendiol, dehydroepiandrosterone, and testosterone.

With continued reference to FIG. 1, genetic biomarker may include CYP19A1 gene that produce enzymes that convert androgens such as androstenedione and testosterone into estrogens including estradiol and estrone. Genetic biomarker may include SRD5A2 gene that aids in production of enzymes that convert testosterone into dihydrotestosterone. Genetic biomarker may include UFT2B17 gene that produces enzymes that metabolize testosterone and dihydrotestosterone. Genetic biomarker may include CYP1A1 gene that produces enzymes that metabolize estrogens into 2 hydroxy-estrogen. Genetic biomarker may include CYP1B1 gene that produces enzymes that metabolize estrogens into 4 hydroxy-estrogen. Genetic biomarker may include CYP3A4 gene that produces enzymes that metabolize estrogen into 16 hydroxy-estrogen. Genetic biomarker may include COMT gene that produces enzymes that metabolize 2 hydroxy-estrogen and 4 hydroxy-estrogen into methoxy estrogen. Genetic biomarker may include GSTT1 gene that produces enzymes that eliminate toxic by-products generated from metabolism of estrogens. Genetic biomarker may include GSTM1 gene that produces enzymes responsible for eliminating harmful by-products generated from metabolism of estrogens. Genetic biomarker may include GSTP1 gene that produces enzymes that eliminate harmful by-products generated from metabolism of estrogens. Genetic biomarker may include SOD2 gene that produces enzymes that eliminate oxidant by-products generated from metabolism of estrogens.

With continued reference to FIG. 1, metabolic, as used herein, includes any process that converts food and nutrition into energy. Metabolic may include biochemical processes that occur within the body. Metabolic biomarker may include blood tests, hair tests, skin tests, amniotic fluid, buccal swabs and/or tissue test to identify a user's metabolism. Metabolic biomarker may include blood tests that examine glucose levels, electrolytes, fluid balance, kidney function, and liver function. Metabolic biomarker may include blood tests that examine calcium levels, albumin, total protein, chloride levels, sodium levels, potassium levels, carbon dioxide levels, bicarbonate levels, blood urea nitrogen, creatinine, alkaline phosphatase, alanine amino transferase, aspartate amino transferase, bilirubin, and the like.

With continued reference to FIG. 1, metabolic biomarker may include blood, saliva, hair, urine, skin, and/or buccal swabs that examine levels of hormones within the body such as 11-hydroxy-androstereone, 11-hydroxy-etiocholanolone, 11-keto-androsterone, 11-keto-etiocholanolone, 16 alpha-hydroxyestrone, 2-hydroxyestrone, 4-hydroxyestrone, 4-methoxyestrone, androstanediol, androsterone, creatinine, DHEA, estradiol, estriol, estrone, etiocholanolone, pregnanediol, pregnanestriol, specific gravity, testosterone, tetrahydrocortisol, tetrahydrocrotisone, tetrahydrodeoxycortisol, allo-tetrahydrocortisol.

With continued reference to FIG. 1, metabolic biomarker may include metabolic rate tests such as breath tests that may analyze a user's resting metabolic rate or number of calories that a user's body burns each day rest. Metabolic biomarker may include one or more vital signs including blood pressure, breathing rate, pulse rate, temperature, and the like. Metabolic biomarker may include blood tests such as a lipid panel such as low density lipoprotein (LDL), high density lipoprotein (HDL), triglycerides, total cholesterol, ratios of lipid levels such as total cholesterol to HDL ratio, insulin sensitivity test, fasting glucose test, Hemoglobin AIC test, adipokines such as leptin and adiponectin, neuropeptides such as ghrelin, pro-inflammatory cytokines such as interleukin 6 or tumor necrosis factor alpha, anti-inflammatory cytokines such as interleukin 10, markers of antioxidant status such as oxidized low-density lipoprotein, uric acid, paraoxonase 1.

With continued reference to FIG. 1, at least a biomarker datum may include a tissue sample analysis correlated to at least a body dimension. Tissue sample as used herein, includes any material extracted from a human body including bodily fluids and tissue. Tissue sample may include for example, blood, urine, sputum, fecal, and solid tissue such as bone or muscle. Tissue sample analysis as used herein, includes any tissue sample analyzed by a laboratory or medical professional such as a medical doctor for examination. In an embodiment, tissue sample analysis may include comparisons of tissue sample examination as compared to reference ranges of normal values or normal findings. For example, tissue sample analysis may include a report identifying strains of bacteria located within a user's gut examined from a stool sample. In yet another non-limiting example, tissue sample analysis may include a report identifying hormone levels of a pre-menopausal female examined from a saliva sample. In yet another non-limiting example, tissue sample analysis may include reported results from a buccal swab that examined genetic mutations of particular genes. In yet another non-limiting example, tissue sample analysis may include a finger-prick blood test that may identify intracellular and extracellular levels of particular nutrients such as Vitamin D, Vitamin C, and Coenzyme Q10.

With continued reference to FIG. 1, a user client device 108 may include, without limitation, a display in communication with at least a server 104; display may include any display as described herein. A user client device 108 may include an additional computing device, such as a mobile device, laptop, desktop computer, or the like; as a non-limiting example, the user client device 108 may be a computer and/or workstation operated by a medical professional. Output may be displayed on at least a user client device 108 using an output graphical user interface 124, as described in more detail below. Transmission to a user client device 108 may include any of the transmission methodologies as described herein.

With continued reference to FIG. 1, at least a server is designed and configured to receive training data. Training data, as used herein, is data containing correlation that a machine-learning process may use to model relationships between two or more categories of data elements. For instance, and without limitation, training data may include a plurality of data entries, each entry representing a set of data elements that were recorded, received, and/or generated together; data elements may be correlated by shared existence in a given data entry, by proximity in a given data entry, or the like. Multiple data entries in training data may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data according to various correlations; correlations may indicate causative and/or predictive links between categories of data elements, which may be modeled as relationships such as mathematical relationships by machine-learning processes as described in further detail below. Training data may be formatted and/or organized by categories of data elements, for instance by associating data elements with one or more descriptors corresponding to categories of data elements. As a non-limiting example, training data may include data entered in standardized forms by persons or processes, such that entry of a given data element in a given field in a form may be mapped to one or more descriptors of categories. Elements in training data may be linked to descriptors of categories by tags, tokens, or other data elements; for instance, and without limitation, training data may be provided in fixed-length formats, formats linking positions of data to categories such as comma-separated value (CSV) formats and/or self-describing formats such as extensible markup language (XML), enabling processes or devices to detect categories of data.

Alternatively or additionally, and still referring to FIG. 1, training data may include one or more elements that are not categorized; that is, training data may not be formatted or contain descriptors for some elements of data. Machine-learning algorithms and/or other processes may sort training data according to one or more categorizations using, for instance, natural language processing algorithms, tokenization, detection of correlated values in raw data and the like; categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name and/or a description of a medical condition or therapy may be identified by reference to a list, dictionary, or other compendium of terms, permitting ad-hoc categorization by machine-learning algorithms, and/or automated association of data in the data entry with descriptors or into a given format. The ability to categorize data entries automatedly may enable the same training data to be made applicable for two or more distinct machine-learning algorithms as described in further detail below.

With continued reference to FIG. 1, at least a server 104 is configured to receive a first training set 112 including a plurality of first data entries, each first data entry of the first training set 112 including at least a first element of first classified biomarker data 116 and at least a correlated compatible substance label 120. At least a first element of first classified biomarker data 116 as used herein, includes any data indicative a person's physiological state that has been classified. Physiological state, as used herein, includes any information or data describing the current condition of a user's body. Classified as used herein, includes any classification system that relates to a dimension of the human body as described above in more detail. For instance and without limitation, biomarker data describing population of a species of bacteria found within the gastrointestinal tract may be classified as microbiome. Biomarker data may be classified into more than one dimension of the human body. For instance and without limitation, biomarker data describing population of a species of bacteria found within the gastrointestinal tract may be classified as microbiome and gut wall. In yet another non-limiting example, biomarker data describing a genetic single nucleotide polymorphism that increases a user's risk of developing diabetes mellitus, may be classified as genetics and metabolism. In an embodiment, first element of classified biomarker data may be received from at least a constitutional analysis. Constitutional analysis as used herein includes any medical procedure or test performed to detect, diagnose, monitor disease, disease processes, susceptibility, and treatment. Constitutional analysis may include any direct to consumer test that a consumer may perform without the need for a medical professional to order the test such as a medical doctor or nurse practitioner. In an embodiment, first element of classified biomarker data may be received from at least a tissue sample analysis. Tissue sample analysis may include any of the tissue sample analysis as described herein.

With continued reference to FIG. 1, a correlated compatible substance label 120 as used herein, includes any element of data identifying and/or describing any food substance that is compatible with a user. Food substance, as used herein, includes any substance consumed to provide nutritional support for an organism such as a human being. Food substance may be of plant or animal origin, and may contain essential nutrients such as carbohydrates, fats, proteins, vitamins, or minerals. Food substance may be categorized into categories based on type of food substance such as vegetables, fruits, grains, proteins, fats, herbs, spices, and other. Food substance may include individual foods such as banana, Brussel sprout, egg, endive, garlic, hazelnut and the like.

With continued reference to FIG. 1, correlated compatible substance label 120 may be associated with one or more elements of classified biomarker data. For example, a correlated compatible substance label 120 for garlic may be associated with one or more classified biomarker datums including for example genetic MTHFR gene mutation type C/T as well as the microbiome microbial strain of *Candida Albicans* found in a stool sample. In yet another non-limiting example, a correlated compatible substance label 120 for chicken breast may be associated with one or more classified biomarker datums including for example, nutrient blood sample showing low serum levels of Vitamin B3 as well as metabolic data reflecting elevated low density lipoprotein (LDL) levels. In yet another non-limiting example, a correlated compatible substance label 120 for mozzarella cheese may be associated with nutrient data showing low intracellular and extracellular calcium as well as genetic data showing a user has A/A variant of MCM6 gene which regulates production of lactase enzyme which is not impaired with the A/A variant.

With continued reference to FIG. 1, biomarker datum and correlated compatible substance label 120 may be stored in any suitable data and/or data type. For instance, and without limitation, correlated compatible substance label 120 may include textual data, such as numerical, character, and/or string data. Textual data may include a standardized name and/or code for a disease, disorder, or the like; codes may include diagnostic codes and/or diagnosis codes, which may include without limitation codes used in diagnosis classification systems such as The International Statistical Classification of Diseases and Related Health Problems (ICD). In general, there is no limitation on forms textual data or non-textual data used as at least a correlated compatible substance label 120 may take; persons skilled in the art, upon reviewing the entirety of this disclosure, will be aware of various forms which may be suitable for use as at least an advisory label consistently with this disclosure.

With continued reference to FIG. 1, correlated compatible substance label 120 may be stored as image data, such as for example an image of a particular food substance such as a photograph of a pear or an image of a steak. Image data may be stored in various forms including for example, joint photographic experts group (JPEG), exchangeable image file format (Exif), tagged image file format (TIFF), graphics interchange format (GIF), portable network graphics (PNG), netpbm format, portable bitmap (PBM), portable any map (PNM), high efficiency image file format (HEIF), still picture interchange file format (SPIFF), better portable graphics (BPG), drawn filed, enhanced compression wavelet (ECW), flexible image transport system (FITS), free lossless image format (FLIF), graphics environment manage (GEM), portable arbitrary map (PAM), personal computer exchange (PCX), progressive graphics file (PGF), gerber formats, 2 dimensional vector formats, 3 dimensional vector formats, compound formats including both pixel and vector data such as encapsulated postscript (EPS), portable document format (PDF), and stereo formats.

With continued reference to FIG. 1, in each first data element of first training set 112 at least a first element of first classified biomarker data 116 is correlated with a compatible substance label 120 where the first element of first classified biomarker data 116 is located in the same data element and/or portion of data element as the compatible substance label 120; for example, and without limitation, an element of classified biomarker data is correlated with a compatible substance label 120 where both element of classified biomarker data and compatible substance label 120 are contained within the same first data element of the first training set 112. As a further example, an element of classified biomarker data is correlated with a correlated compatible substance label 120 where both share a category label as described in further detail below, where each is within a certain distance of the other within an ordered collection of data in data element, or the like. Still further, an element of classified biomarker data may be correlated with a correlated compatible substance label 120 where the element of classified biomarker data and the correlated compatible substance label 120 share an origin, such as being data that was collected with regard to a single person or the like. In an embodiment, a first datum may be more closely correlated with a second datum in the same data element than with a third datum contained in the same data element; for instance, the first element and the second element may be closer to each other in an ordered set of data than either is to the third element, the first element and second element may be contained in the same subdivision and/or section of data while the third element is in a different subdivision and/or section of data, or the like. Persons skilled in the art, upon reviewing the entirety of this disclosure, will be aware of various forms and/or degrees of correlation between classified biomarker data and correlated compatible substance label 120 that may exist in first training set 112 and/or first data element consistently with this disclosure.

With continued reference to FIG. 1, at least a server 104 may be designed and configured to associate at least an element of classified biomarker data with at least a category from a list of significant categories of classified biomarker data. Significant categories of classified biomarker data may include labels and/or descriptors describing types of classified biomarker data that are identified as being of high relevance in identifying compatible substance label 120. As a non-limiting example, one or more categories may identify significant categories of classified biomarker data based on degree of diagnostic relevance to one or more impactful body dimensions and/or within one or more medical or public health fields. For instance, and without limitation, a particular set of biomarkers, test results, and/or biochemical information may be recognized in a given medical field as useful for identifying various conditions or associated food substances that may be compatible with a particular condition as well as associated ingredients and food substances that may not be compatible with a particular condition. As a non-limiting example, and without limitation, biomarker data describing disorders associated with vegetarian diets such as elevated fasting blood sugar levels may be useful in selecting compatible substance label 120 that include fruits, vegetables, grains, and dairy and that avoid fish or meat. As an additional example, biomarker data associated with dyslipidemia such as the presence of APOE 4 gene or mutations of APOA2 gene may be useful in selecting compatible substance label 120 that do not contain saturated fat such as coconut oil and palm oil. In a further non-limiting example, biomarker data describing disorders of AMY1 gene that produce enzymes that digest starchy foods may be useful in selecting compatible substance label 120 that are free of starches including for example nuts such as almonds and hazelnuts, and non-starchy vegetables such as artichokes, asparagus, bean sprouts, Brussel sprouts, broccoli, cabbage and the like. Persons skilled in the art, upon reviewing the entirety of this disclosure, will be aware of various additional categories of biological data that may be used consistently with this disclosure.

Still referring to FIG. 1, at least a server 104 may receive the list of significant categories according to any suitable process; for instance, and without limitation, at least a server 104 may receive the list of significant categories from at least an expert. In an embodiment, at least a server 104 may provide a graphical user interface 124, which may include without limitation a form or other graphical element having data entry fields, wherein one or more experts, including without limitation clinical and/or scientific experts, may enter information describing one or more categories of biomarker data that the experts consider to be significant or useful for detection of conditions; fields in graphical user interface 124 may provide options describing previously identified categories, which may include a comprehensive or near-comprehensive list of types of biomarker data detectable using known or recorded testing methods, for instance in "drop-down" lists, where experts may be able to select one or more entries to indicate their usefulness and/or significance in the opinion of the experts. Fields may include free-form entry fields such as text-entry fields where an expert may be able to type or otherwise enter text, enabling expert to propose or suggest categories not currently recorded. First graphical user interface 124 or the like may include fields corresponding to correlated compatible substance label 120, where experts may enter data describing compatible substance label 120 and/or categories of compatible substance label 120 the experts consider related to entered categories of biomarker data; for instance, such fields may include drop-down lists or other pre-populated data entry fields listing currently recorded compatible substance label 120, and which may be comprehensive, permitting each expert to select a compatible substance label 120 and/or a plurality of compatible substance label 120 the expert believes to be predicted and/or associated with each category of classified biomarker data selected by the expert. Fields for entry of compatible substance label 120 and/or categories of compatible substance label 120 may include free-form data entry fields such as text entry fields; as described above, examiners may enter data not presented in pre-populated data fields in the free-form data entry fields. Alternatively or additionally, fields for entry of compatible substance label 120 may enable an expert to select and/or enter information describing or linked to a category of compatible substance label 120 that the expert considers significant, where significance may indicate likely impact on longevity, mortality, quality of life, or the like as described in further detail below. First graphical user interface 124 may provide an expert with a field in which to indicate a reference to a document describing significant categories of biomarker data, relationships of such categories to compatible substance label 120, and/or significant categories of compatible substance label 120. Any data described above may alternatively or additionally be received from experts similarly organized in paper form, which may be captured and entered into data in a similar way, or in a textual form such as a portable document file (PDF) with examiner entries, or the like.

With continued reference to FIG. 1, data information describing significant categories of biomarker data, relationships of such categories to compatible substance label 120, and/or significant categories of compatible substance label 120 may alternatively or additionally be extracted from one or more documents using a language processing module 128. Language processing module 128 may include any hardware and/or software module. Language processing module 128 may be configured to extract, from the one or more documents, one or more words. One or more words may include, without limitation, strings of one or characters, including without limitation any sequence or sequences of letters, numbers, punctuation, diacritic marks, engineering symbols, geometric dimensioning and tolerancing (GD&T) symbols, chemical symbols and formulas, spaces, whitespace, and other symbols, including any symbols usable as textual data as described above. Textual data may be parsed into tokens, which may include a simple word (sequence of letters separated by whitespace) or more generally a sequence of characters as described previously. The term "token," as used herein, refers to any smaller, individual groupings of text from a larger source of text; tokens may be broken up by word, pair of words, sentence, or other delimitation. These tokens may in turn be parsed in various ways. Textual data may be parsed into words or sequences of words, which may be considered words as well. Textual data may be parsed into "n-grams", where all sequences of n consecutive characters are considered. Any or all possible sequences of tokens or words may be stored as "chains", for example for use as a Markov chain or Hidden Markov Model Still referring to FIG. 1, language processing module 128 may compare extracted words to categories of biomarker data recorded by at least a server 104, and/or one or more categories of compatible substance label 120 recorded by at least a server 104; such data for comparison may be entered on at least a server 104 as described above using expert data inputs or the like. In an embodiment, one or more categories may be enumerated, to find total count of mentions in such documents. Alternatively or additionally, language processing module 128 may operate to produce a language processing model. Language processing model may include a program automatically generated by at least a server 104 and/or language processing module 128 to produce associations between one or more words extracted from at least a document and detect associations, including without limitation mathematical associations, between such words, and/or associations of extracted words with categories of classified biomarker data, relationships of such categories to compatible substance label 120, and/or categories of compatible substance label 120. Associations between language elements, where language elements include for purposes herein extracted words, categories of classified biomarker data, relationships of such categories to compatible substance label 120, and/or categories of compatible substance label 120 may include, without limitation, mathematical associations, including without limitation statistical correlations between any language element and any other language element and/or language elements. Statistical correlations and/or mathematical associations may include probabilistic formulas or relationships indicating, for instance, a likelihood that a given extracted word indicates a given category of classified biomarker data, a given relationship of such categories to compatible substance label 120, and/or a given category of compatible substance label 120. As a further example, statistical correlations and/or mathematical associations may include probabilistic formulas or relationships indicating a positive and/or negative association between at least an extracted word and/or a given category of classified biomarker data, a given relationship of such categories to compatible substance label 120, and/or a given category of compatible substance label 120; positive or negative indication may include an indication that a given document is or is not indicating a category of classified biomarker data, relationship of such category to compatible substance label 120, and/or category of compatible substance label 120 is or is not significant. For instance, and without limitation, a negative indication may be determined from a phrase such as "*Bacteroides* species were not found to alter carbohydrate metabolism," whereas a positive indication may be determined from a phrase such as "*Lactobacillus* species were found to alter carbohydrate metabolism" as an illustrative example; whether a phrase, sentence, word, or other textual element in a document or corpus of documents constitutes a positive or negative indicator may be determined, in an embodiment, by mathematical associations between detected words, comparisons to phrases and/or words indicating positive and/or negative indicators that are stored in memory by at least a server 104, or the like.

Still referring to FIG. 1, language processing module 128 and/or at least a server 104 may generate the language processing model by any suitable method, including without limitation a natural language processing classification algorithm; language processing model may include a natural language process classification model that enumerates and/or derives statistical relationships between input term and output terms. Algorithm to generate language processing model may include a stochastic gradient descent algorithm, which may include a method that iteratively optimizes an objective function, such as an objective function representing a statistical estimation of relationships between terms, including relationships between input terms and output terms, in the form of a sum of relationships to be estimated. In an alternative or additional approach, sequential tokens may be modeled as chains, serving as the observations in a Hidden Markov Model (HMM). HMMs as used herein, are statistical models with inference algorithms that that may be applied to the models. In such models, a hidden state to be estimated may include an association between an extracted word category of physiological data, a given relationship of such categories to compatible substance label 120, and/or a given category of compatible substance label 120. There may be a finite number of category of physiological data, a given relationship of such categories to compatible substance label 120, and/or a given category of compatible substance label 120 to which an extracted word may pertain; an HMM inference algorithm, such as the forward-backward algorithm or the Viterbi algorithm, may be used to estimate the most likely discrete state given a word or sequence of words. Language processing module 128 may combine two or more approaches. For instance, and without limitation, machine-learning program may use a combination of Naive-Bayes (NB), Stochastic Gradient Descent (SGD), and parameter grid-searching classification techniques; the result may include a classification algorithm that returns ranked associations.

Continuing to refer to FIG. 1, generating language processing model may include generating a vector space, which may be a collection of vectors, defined as a set of mathematical objects that can be added together under an operation of addition following properties of associativity, commutativity, existence of an identity element, and existence of an inverse element for each vector, and can be multiplied by scalar values under an operation of scalar multiplication compatible with field multiplication, and that has an identity element is distributive with respect to vector addition, and is distributive with respect to field addition. Each vector in an n-dimensional vector space may be represented by an n-tuple of numerical values. Each unique extracted word and/or language element as described above may be represented by a vector of the vector space. In an embodiment, each unique extracted and/or other language element may be represented by a dimension of vector space; as a non-limiting example, each element of a vector may include a number representing an enumeration of co-occurrences of the word and/or language element represented by the vector with another word and/or language element. Vectors may be normalized, scaled according to relative frequencies of appearance and/or file sizes. In an embodiment associating language elements to one another as described above may include computing a degree of vector similarity between a vector representing each language element and a vector representing another language element; vector similarity may be measured according to any norm for proximity and/or similarity of two vectors, including without limitation cosine similarity, which measures the similarity of two vectors by evaluating the cosine of the angle between the vectors, which can be computed using a dot product of the two vectors divided by the lengths of the two vectors.

Degree of similarity may include any other geometric measure of distance between vectors.

Still referring to FIG. 1, language processing module 128 may use a corpus of documents to generate associations between language elements in a language processing module 128 and at least a server 104 may then use such associations to analyze words extracted from one or more documents and determine that the one or more documents indicate significance of a category of classified biomarker data, a given relationship of such categories to compatible substance label 120, and/or a given category of compatible substance label 120. In an embodiment, at least a server 104 may perform this analysis using a selected set of significant documents, such as documents identified by one or more experts as representing good science, good clinical analysis, or the like; experts may identify or enter such documents via graphical user interface 124, or may communicate identities of significant documents according to any other suitable method of electronic communication, or by providing such identity to other persons who may enter such identifications into at least a server 104. Documents may be entered into at least a server 104 by being uploaded by an expert or other persons using, without limitation, file transfer protocol (FTP) or other suitable methods for transmission and/or upload of documents; alternatively or additionally, where a document is identified by a citation, a uniform resource identifier (URI), uniform resource locator (URL) or other datum permitting unambiguous identification of the document, at least a server 104 may automatically obtain the document using such an identifier, for instance by submitting a request to a database or compendium of documents such as JSTOR as provided by Ithaka Harbors, Inc. of New York.

Continuing to refer to FIG. 1, whether an entry indicating significance of a category of classified biomarker data, a given relationship of such categories to compatible substance label 120, and/or a given category of compatible substance label 120 is entered via graphical user interface 124, alternative submission means, and/or extracted from a document or body of documents as described above, an entry or entries may be aggregated to indicate an overall degree of significance. For instance, each category of classified biomarker data, relationship of such categories to compatible substance label 120, and/or category of compatible substance label 120 may be given an overall significance score; overall significance score may, for instance, be incremented each time an expert submission and/or paper indicates significance as described above. Persons skilled in the art, upon reviewing the entirety of this disclosure will be aware of other ways in which scores may be generated using a plurality of entries, including averaging, weighted averaging, normalization, and the like. Significance scores may be ranked; that is, all categories of classified biomarker data, relationships of such categories to compatible substance label 120, and/or categories of compatible substance label 120 may be ranked according significance scores, for instance by ranking categories of classified biomarker data, relationships of such categories to compatible substance label 120, and/or categories of compatible substance label 120 higher according to higher significance scores and lower according to lower significance scores. Categories of classified biomarker data, relationships of such categories to compatible substance label 120, and/or categories of compatible substance label 120 may be eliminated from current use if they fail a threshold comparison, which may include a comparison of significance score to a threshold number, a requirement that significance score belong to a given portion of ranking such as a threshold percentile, quartile, or number of top-ranked scores. Significance scores may be used to filter outputs as described in further detail below; for instance, where a number of outputs are generated and automated selection of a smaller number of outputs is desired, outputs corresponding to higher significance scores may be identified as more probable and/or selected for presentation while other outputs corresponding to lower significance scores may be eliminated. Alternatively or additionally, significance scores may be calculated per sample type; for instance, entries by experts, documents, and/or descriptions of purposes of a given type of biomarker data or sample collection as described above may indicate that for that type of biomarker data or sample collection a first category of classified biomarker data, relationship of such category to compatible substance label 120, and/or category of compatible substance label 120 is significant with regard to that test, while a second category of classified biomarker data, relationship of such category to compatible substance label 120, and/or category of compatible substance label 120 is not significant; such indications may be used to perform a significance score for each category of classified biomarker data, relationship of such category to compatible substance label 120, and/or category of compatible substance label 120 is or is not significant per type of classified biomarker sample, which may then may be subjected to ranking, comparison to thresholds and/or elimination as described above.

Still referring to FIG. 1, at least a server 104 may detect further significant categories of classified biomarker data, relationships of such categories to compatible substance label 120, and/or categories of compatible substance label 120 using machine-learning processes, including without limitation unsupervised machine-learning processes as described in further detail below; such newly identified categories, as well as categories entered by experts in free-form fields as described above, may be added to pre-populated lists of categories, lists used to identify language elements for language learning module, and/or lists used to identify and/or score categories detected in documents, as described above.

Continuing to refer to FIG. 1, in an embodiment, at least a server 104 may be configured, for instance as part of receiving the first training set 112, to associate at least a correlated first compatible substance label 120 with at least a category from a list of significant categories of compatible substance label 120. Significant categories of compatible substance label 120 may be acquired, determined, and/or ranked as described above. As a non-limiting example, compatible substance label 120 may be organized according to relevance to and/or association with a list of significant conditions. A list of significant conditions may include, without limitation, conditions having generally acknowledged impact on longevity and/or quality of life; this may be determined, as a non-limiting example, by a product of relative frequency of a condition within the population with years of life and/or years of able-bodied existence lost, on average, as a result of the condition. A list of conditions may be modified for a given person to reflect a family history of the person; for instance, a person with a significant family history of a particular condition or set of conditions, or a genetic profile having a similarly significant association therewith, may have a higher probability of developing such conditions than a typical person from the general population, and as a result at least a server 104 may modify list of significant categories to reflect this difference.

With continued reference to FIG. 1, at least a server 104 may be designed and configured to receive a second training set 132 including a plurality of second data entries. Each second data entry of the second training set 132 including at least a second element of second classified biomarker data 136 and at least a correlated compatible substance label 120. Second classified biomarker data 136 as used herein, may include any biomarker data that has been classified to a second dimension of the human body that may be separate from a first dimension of the human body. Dimension of the human body may include any of the dimensions of the human body as described above, including epigenetics, gut wall, microbiome, nutrients, genetics, and metabolism. For example and without limitation, where first classified biomarker data 116 may be classified to epigenetics, second classified biomarker data 136 may be classified to gut wall. In yet another non-limiting example, where first classified biomarker data 116 may be classified to microbiome, second classified biomarker data 136 may be classified to genetics. Correlation may include any correlation suitable for correlation of a first element of first classified biomarker data 116 and at least a correlated compatible substance label 120. Each second data entry of the second training set 132 includes at least a compatible substance label 120; at least a compatible substance label 120 may include any label suitable for use as compatible substance label 120 as described above.

With continued reference to FIG. 1, at least a server 104 may be configured, for instance as part of receiving second training set 132, to associate a compatible substance label 120 with at least a category from a list of significant categories of compatible substance label 120. This may be performed as described above for use of lists of significant categories with regard to first training set 112. Significance may be determined, and/or association with at least a category, may be performed for first training set 112 according to a first process as described above and for second training set 132 according to a second process.

With continued reference to FIG. 1, at least a server 104 may be configured, for instance as part of receiving second training set 132, to associate at least a correlated compatible substance label 120 with at least a category from a list of significant categories of compatible substance category labels. This may be done using expert input and utilizing any of the methodology as described above in reference to first training set 112.

With continued reference to FIG. 1, at least a server 104 may be configured to receive component elements of training sets and utilize components to generate machine-learning models to select at least a compatible substance. Components may include individual training sets relating each of the six different body dimensions to correlated compatible substance label 120. For example and without limitation, at least a server 104 may be configured to receive a third training set including a plurality of third data entries, each third data entry of the plurality of third data entries including at least a third element of third classified biomarker data and at least a correlated compatible substance label 120. For example and without limitation, at least a server 104 may be configured to receive a fourth training set including a plurality of fourth data entries, each fourth data entry of the plurality of fourth data entries including at least a fourth element of fourth classified biomarker data and at least a correlated compatible substance label 120. For example and without limitation, at least a server 104 may be configured to receive a fifth training set including a plurality of fifth data entries, each fifth data entry of the plurality of fifth data entries including at least a fifth element of fifth classified biomarker data and at least a correlated compatible substance label 120. For example and without limitation, at least a server 104 may be configured to receive a sixth training set including a plurality of sixth data entries, each sixth data entry of the plurality of sixth data entries including at least a sixth element of sixth classified biomarker data and at least a correlated compatible substance label 120. At least a server 104 may receive training sets from training set database 140, as described below in more detail in reference to FIG. 6.

With continued reference to FIG. 1, at least a server 104 may be configured to receive component elements of training sets to generate machine-learning models to select at least a compatible substance label 120. Component elements of training sets may include training sets containing sub-sets of dimensional biomarker data related to correlated compatible substance label 120. For instance and without limitation, a first training set 112 including a first element of first classified biomarker data 116 relating to microbiome dimension may contain component elements with component elements containing sub-sets within dimension. In such an instance, microbiome dimension may be composed of component training sets that establish relations between sub-categories of microbiome biomarker data and compatible substance label 120. For instance and without limitation, microbiome dimension may include component training sets such as bacterial strains and compatible substance label 120, archaea strains and compatible substance label 120, fungi strains and compatible substance label 120, lactose breath tests and compatible substance label 120, methane breath tests and compatible substance label 120, fructose breath tests and compatible labels, stool cultures and compatible substance label 120 and the like.

With continued reference to FIG. 1, at least a server may be configured to select at least a first machine-learning model 148 as a function of the first training set 112 and the at least a biomarker datum. A machine learning process is a process that automately uses a body of data known as "training data" and/or a "training set" to generate an algorithm that will be performed by a computing device/module to produce outputs given data provided as inputs; this is in contrast to a non-machine learning software program where the commands to be executed are determined in advance by a user and written in a programming language.

With continued reference to FIG. 1, at least a server 104 may include at least a label learner 144, the at least a label learner 144 designed and configured to select at least a first machine-learning model 148 as a function of the first training set 112 and the at least a biomarker datum. At least a label learner 144 may include any hardware and/or software module. At least a label learner 144 is designed and configured to generate at least a compatible substance instruction set using the at least a biomarker datum, the first training set 112, and the at least a first machine-learning algorithm. A machine learning process is a process that automately uses a body of data known as "training data" and/or a "training set" to generate an algorithm that will be performed by a computing device/module to produce outputs given data provided as inputs; this is in contrast to a non-machine learning software program where the commands to be executed are determined in advance by a user and written in a programming language.

With continued reference to FIG. 1, at least a server 104 and/or at least a label learner 144 may be designed and configured to generate at least a first machine learning module using the first training set wherein the first machine-learning model outputs at least a compatible substance containing at least a compatible substance index value as a function of relating the at least a user biomarker datum to at least a compatible substance using the first training set and the at least a first machine-learning model. At least a first machine-learning model 148 may include one or more models that determine a mathematical relationship between biomarker data and compatible substance label 120. Such models may include without limitation model developed using linear regression models. Linear regression models may include ordinary least squares regression, which aims to minimize the square of the difference between predicted outcomes and actual outcomes according to an appropriate norm for measuring such a difference (e.g. a vector-space distance norm); coefficients of the resulting linear equation may be modified to improve minimization. Linear regression models may include ridge regression methods, where the function to be minimized includes the least-squares function plus term multiplying the square of each coefficient by a scalar amount to penalize large coefficients. Linear regression models may include least absolute shrinkage and selection operator (LASSO) models, in which ridge regression is combined with multiplying the least-squares term by a factor of 1 divided by double the number of samples. Linear regression models may include a multi-task lasso model wherein the norm applied in the least-squares term of the lasso model is the Frobenius norm amounting to the square root of the sum of squares of all terms. Linear regression models may include the elastic net model, a multi-task elastic net model, a least angle regression model, a LARS lasso model, an orthogonal matching pursuit model, a Bayesian regression model, a logistic regression model, a stochastic gradient descent model, a perceptron model, a passive aggressive algorithm, a robustness regression model, a Huber regression model, or any other suitable model that may occur to persons skilled in the art upon reviewing the entirety of this disclosure. Linear regression models may be generalized in an embodiment to polynomial regression models, whereby a polynomial equation (e.g. a quadratic, cubic or higher-order equation) providing a best predicted output/actual output fit is sought; similar methods to those described above may be applied to minimize error functions, as will be apparent to persons skilled in the art upon reviewing the entirety of this disclosure.

With continued reference to FIG. 1, at least a learner may select at least a first machine-learning model 148 from a machine-learning model database 152. This may be done as described below in more detail in reference to FIG. 7. First machine-learning model 148 may be selected as a function of the at least a first element of first classified biomarker datum contained within the first training set as described below in more detail in reference to FIG. 7.

With continued reference to FIG. 1, at least a server 104 is configured to generate at least a compatible substance instruction set containing at least a compatible substance ranked as a function of the at least a compatible substance index value. Compatible substance instruction set may include a list of compatible substances, each containing a score indicating a particular percentage and/or indication of compatibility with a particular user. For example, a compatible substance may include a ranking that may include categories of compatible substances as described below in more detail in reference to FIG. 11.

With continued reference to FIG. 1, machine-learning algorithms may generate compatible substance instruction sets as a function of a classification of at least a compatible substance. Classification as used herein includes pairing or grouping of compatible substance label 120 as a function of a shared commonality. Classification may include for example, groupings, pairings, and/or trends between biomarker data and current compatible substance label 120, future compatible substance label 120, and the like. Machine-learning algorithms may include any and all algorithms as performed by any modules, described herein for at least a label learner 144. For example, machine-learning algorithms may relate fasting blood glucose readings of a user to user's future propensity to need to eliminate high starch foods. Machine-learning algorithms may examine precursor condition and future propensity to eliminate or necessitate consumption of a particular compatible element. For example, machine-learning algorithms may examine a user with a gene that codes for lactase insufficiency and future propensity to not be able to consume hard cheeses with low lactase quantities. Machine-learning algorithms may examine related food intolerances such as users who lack *Bacteroides* species and inability to digest dairy products as well as users who lack *Lactobacillus* species and inability to digest dairy products. Machine-learning algorithms may examine development of subsequent food recommendations. For example, machine-learning algorithms may examine low salivary progesterone and addition of sweet potatoes and subsequent addition of pumpkin after subsequent salivary tests reveal continued low progesterone levels.

Continuing to refer to FIG. 1, machine-learning algorithm used to generate first machine-learning model 148 may include, without limitation, linear discriminant analysis. Machine-learning algorithm may include quadratic discriminate analysis. Machine-learning algorithms may include kernel ridge regression. Machine-learning algorithms may include support vector machines, including without limitation support vector classification-based regression processes. Machine-learning algorithms may include stochastic gradient descent algorithms, including classification and regression algorithms based on stochastic gradient descent. Machine-learning algorithms may include nearest neighbors' algorithms. Machine-learning algorithms may include Gaussian processes such as Gaussian Process Regression. Machine-learning algorithms may include cross-decomposition algorithms, including partial least squares and/or canonical correlation analysis. Machine-learning algorithms may include naïve Bayes methods. Machine-learning algorithms may include algorithms based on decision trees, such as decision tree classification or regression algorithms. Machine-learning algorithms may include ensemble methods such as bagging meta-estimator, forest of randomized tress, AdaBoost, gradient tree boosting, and/or voting classifier methods. Machine-learning algorithms may include neural net algorithms, including convolutional neural net processes.

Still referring to FIG. 1, at least a label learner 144 may generate compatible substance label 120 using alternatively or additional artificial intelligence methods, including without limitation by creating an artificial neural network, such as a convolutional neural network comprising an input layer of nodes, one or more intermediate layers, and an output layer of nodes. Connections between nodes may be created via the process of "training" the network, in which elements from a training dataset are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning This network may be trained using any training set as described herein; the trained network may then be used to apply detected relationships between elements of classified biomarker data and compatible substance label 120.

With continued reference to FIG. 1, generating at least a compatible substance instruction set may include retrieving at least a compatible substance index value from compatible substance index value database 156 and generating at least a compatible substance instruction set as a function of the at least a compatible substance index value. Compatible substance index value as used herein, is a value assigned to a compatible substance indicating a degree of compatibility between a first compatible element and a second compatible element for a user with any given biomarker datum. In an embodiment, compatible substance index value may be stored in a database or datastore as described below in more detail in reference to FIG. 10. In an embodiment, compatible substance index value scores may be calculated based on correlations between compatible substance category, compatible substance biochemistry, and impact of compatible substance on any given biomarker. In an embodiment, compatible substance index value may be ranked whereby a high compatible substance index value between any two compatible substances may indicate that for any two compatible substances a large percentage of individuals with a particular biomarker who tolerated a first compatible substance were able to then tolerate a second compatible substance. A low compatible substance index value between any two compatible elements may indicate that for any two compatible elements a small percentage of individuals with a particular biomarker who tolerated a first compatible substance were unable to then tolerate a second compatible substance. In an embodiment, a compatible substance index value may be evaluated as a function as a function of at least a biomarker datum from a user. For example, a compatible substance index value may contain a high index value for a first biomarker and a low index value for a second biomarker. Generating at least a compatible substance instruction set may include selecting a first compatible substance as a function of a first compatible substance index value and selecting at least a second compatible substance as a function of the first compatible substance index value and the second compatible substance index value.

Figure 2:
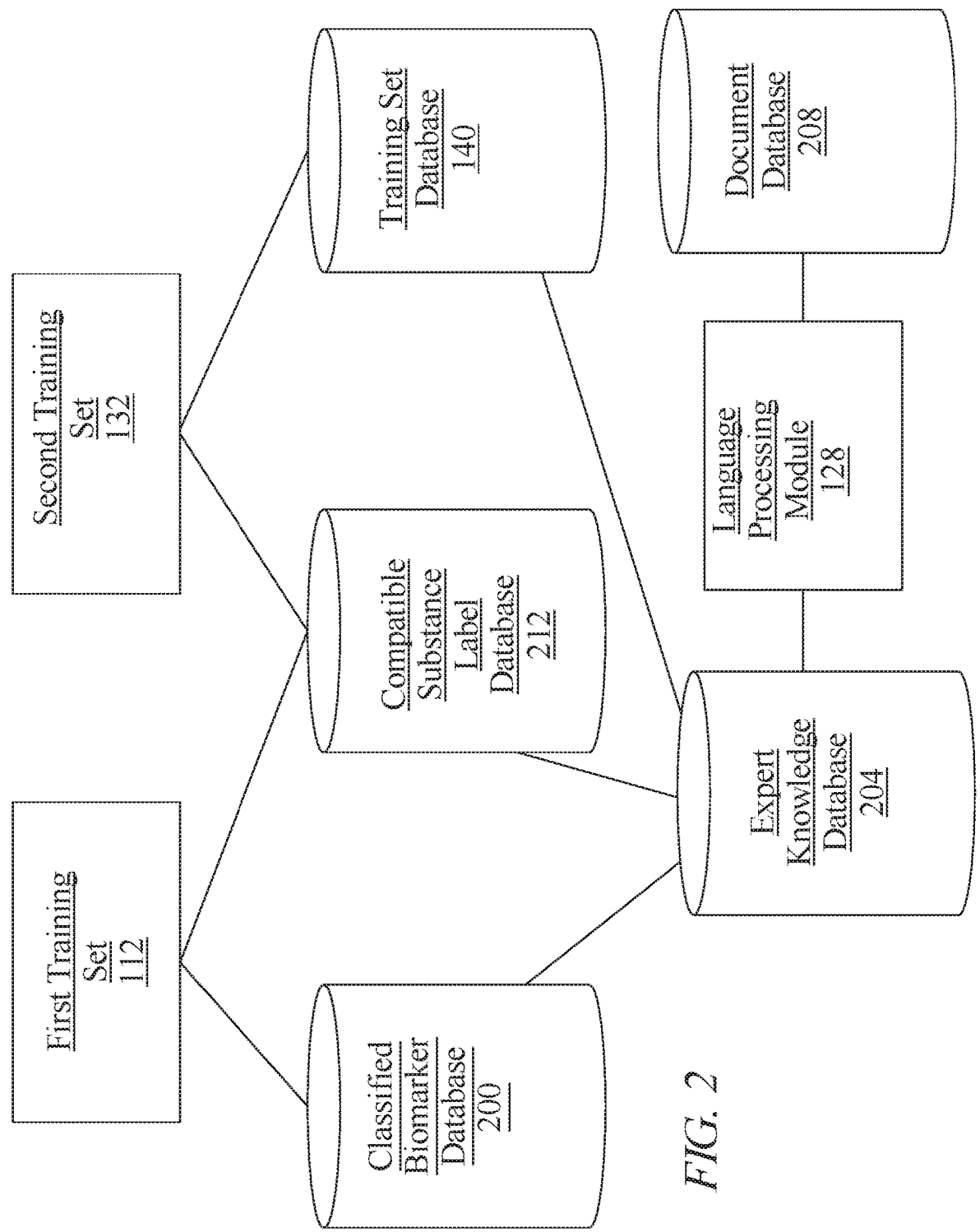
FIG. 2 is a block diagram illustrating embodiments of data storage facilities for use in disclosed systems and methods.

Referring now to FIG. 2, data incorporated in first training set 112 and/or second training set 132 may be incorporated in one or more databases. As a non-limiting example, one or elements of classified biomarker data may be stored in and/or retrieved from a classified biomarker database 200. A classified biomarker database 200 may include any data structure for ordered storage and retrieval of data, which may be implemented as a hardware or software module. A classified biomarker database 200 may be implemented, without limitation, as a relational database, a key-value retrieval datastore such as a NOSQL database, or any other format or structure for use as a datastore that a person skilled in the art would recognize as suitable upon review of the entirety of this disclosure. A classified database 200 may include a plurality of data entries and/or records corresponding to elements of biomarker data as described above. Data entries and/or records may describe, without limitation, data concerning particular biological samples that have been collected; entries may describe reasons for collection of samples, such as without limitation one or more conditions being tested for, which may be listed with related body dimensions. Data entries may include compatible substance label 120 and/or other descriptive entries describing results of evaluation of past physiological data, including results of evaluation by experts including any of the experts as described herein. Such conclusions may have been generated by system 100 in previous iterations of methods, with or without validation of correctness by medical professionals. Data entries in classified biomarker database 200 may be flagged with or linked to one or more additional elements of information, which may be reflected in data entry cells and/or in linked tables such as tables related by one or more indices in a relational database; one or more additional elements of information may include data associating a biomarker sample and/or a person from whom a biomarker sample was extracted or received with one or more cohorts, including demographic groupings such as ethnicity, sex, age, income, geographical region, or the like, one or more common traits or physiological attributes shared with other persons having physiological samples reflected in other data entries, or the like. Additional elements of information may include one or more classified categories of biomarker data as described above. Additional elements of information may include descriptions of particular methods used to obtain physiological samples, such as without limitation physical extraction of blood samples or the like, capture of data with one or more sensors, and/or any other information concerning provenance and/or history of data acquisition. Persons skilled in the art, upon reviewing the entirety of this disclosure, will be aware of various ways in which data entries in a classified biomarker database 200 may reflect categories, cohorts, and/or populations of data consistently with this disclosure.

With continued reference to FIG. 2, at least a server 104 and/or another device in system 100 may populate one or more fields in classified biomarker database 200 using expert information, which may be extracted or retrieved from an expert knowledge database 204. An expert knowledge database 204 may include any data structure and/or data store suitable for use as a biomarker database 200 as described above. Expert knowledge database 204 may include data entries reflecting one or more expert submissions of data such as may have been submitted according to any process described above in reference to FIG. 1, including without limitation by using graphical user interface 124 112. Expert knowledge database may include one or more fields generated by language processing module 128, such as without limitation fields extracted from one or more documents as described above. For instance, and without limitation, one or more categories of biomarker data and/or related compatible substance label 120 and/or categories of compatible substance label 120 associated with an element of classified biomarker data as described above may be stored in generalized from in an expert knowledge database 204 and linked to, entered in, or associated with entries in a biomarker database 200. Documents may be stored and/or retrieved by at least a server 104 and/or language processing module 128 in and/or from a document database 208; document database 208 may include any data structure and/or data store suitable for use as biomarker database 200 as described above. Documents in document database 208 may be linked to and/or retrieved using document identifiers such as URI and/or URL data, citation data, or the like: persons skilled in the art, upon reviewing the entirety of this disclosure, will be aware of various ways in which documents may be indexed and retrieved according to citation, subject matter, author, date, or the like as consistent with this disclosure.

With continued reference to FIG. 2, a compatible substance label 120 database 212, which may be implemented in any manner suitable for implementation of classified biomarker database 200, may be used to store compatible substance label 120 used in system 100, including any compatible substance label 120 correlated with elements of first classified biomarker data 116 utilized in first training set 112 as described above; compatible substance label 120 may be linked to or refer to entries in classified biomarker database 200 to which compatible substance label 120 correspond. Linking may be performed by reference to historical data concerning biomarkers, such as a data entry in classified biomarker database 200 may be determined by reference to a record in an expert knowledge database 204 linking a given compatible substance label 120 to a given category of biomarker data as described above. Entries in compatible substance label 120 database 212 may be associated with one or more categories of compatible substance label 120 as described above, for instance using data stored in and/or extracted from an expert knowledge database 204.

Figure 3:
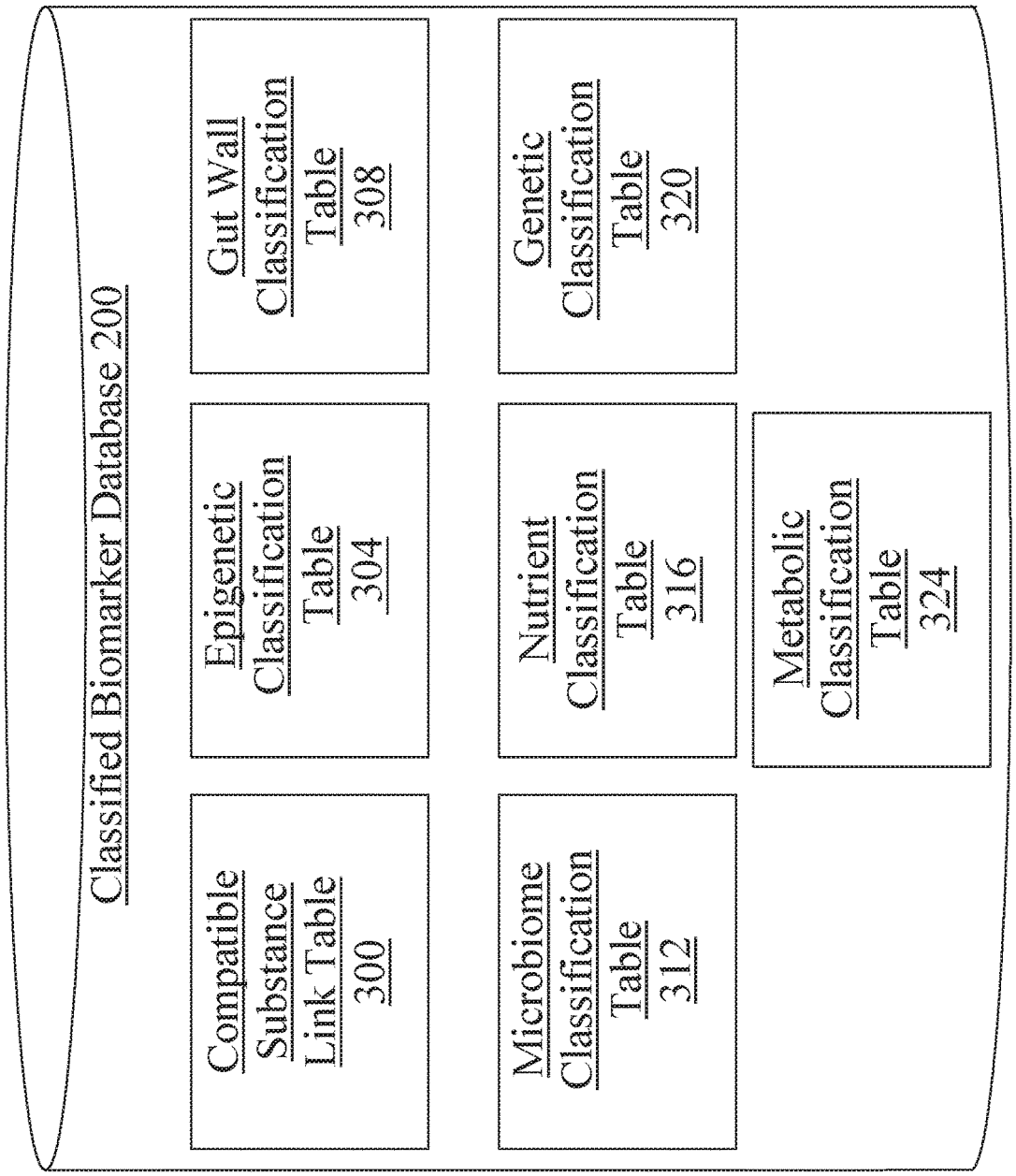
FIG. 3 is a block diagram illustrating an exemplary embodiment of a classified biomarker database.

Referring now to FIG. 3, an exemplary embodiment of classified biomarker database 200 is illustrated. Classified biomarker database 200 may include tables listing one or more biomarkers classified according to body dimension. For instance and without limitation, classified biomarker database 200 may include compatible substance link table 300, which may contain information linking compatible substances to classified biomarkers. For instance, and without limitation, biomarker database 200 may include an epigenetic classification table 304 listing biomarkers classified as epigenetic dimension, such as without limitation data describing phenotype biomarkers, behavioral phenotypes, and methylation state of genetic material. As another non-limiting example, biomarker database 200 may include a gut wall classification table 308, which may list biomarkers classified as gut wall dimension, such as without limitation data describing creatinine levels, lactulose levels, zonulin levels, endotoxin lipopolysaccharide (LPS) and the like. As a further non-limiting example, biomarker database 200 may include a microbiome classification table 312, which may list biomarkers classified as microbiome dimension, such as without limitation sequences of microbes found on or within different surfaces of the body as well as data describing current microbe activity. As a further example, also non-limiting, biomarker database 200 may include a nutrient classification table 316, which may list biomarkers classified as nutrient dimension, including without limitation data describing intra and extra cellular concentrations in white and red blood cells of different vitamins, and micronutrients. As a further non-limiting example, classified biomarker database 200 may include genetic classification table 320, which may list biomarkers classified as genetic dimension, such as without limitation data describing partial or entire sequences of genetic material and genetic mutations. As a further non-limiting example, classified biomarker database 200 may include metabolic classification table 324, which may list biomarkers classified as metabolic dimension including for example blood, salivary, hair, skin, urine, and buccal swabs indicating current hormone states, current metabolic rate, and the like. Tables presented above are presented for exemplary purposes only; persons skilled in the art will be aware of various ways in which data may be organized in biomarker database 200 consistently with this disclosure.

Figure 4:
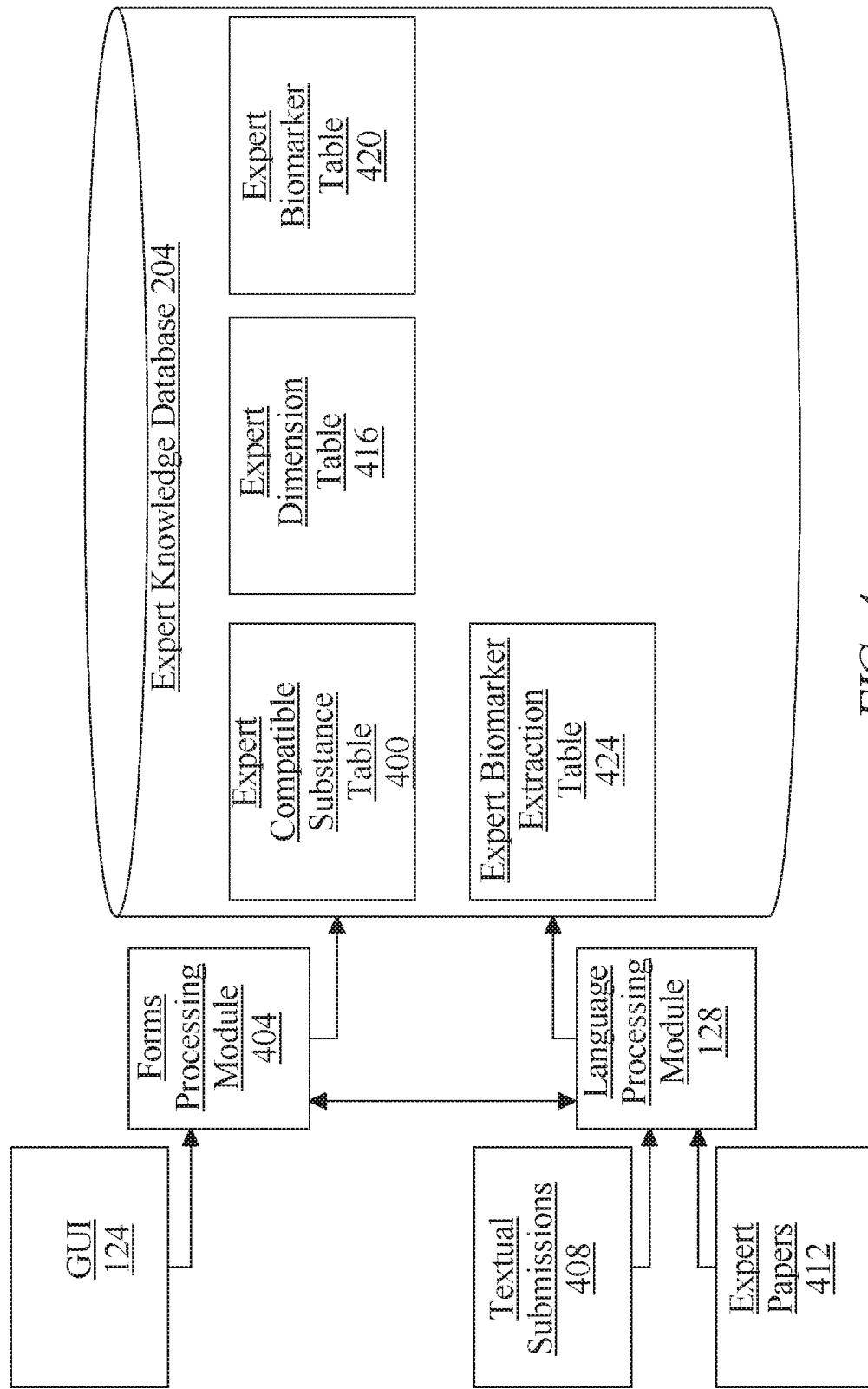
FIG. 4 is a block diagram illustrating an exemplary embodiment of an expert knowledge database.

Referring now to FIG. 4, an exemplary embodiment of expert knowledge database 204 is illustrated. One or more database tables in expert knowledge database 204 may include, as a non-limiting example, an expert compatible substance table 400. Expert compatible substance table 400 may be a table relating classified biomarker data as described above to expert compatible substance label 120; for instance, where an expert has entered data relating a compatible substance label 120 to a category of classified biomarker data and/or to an element of classified biomarker data via graphical user interface 124 as described above, one or more rows recording such an entry may be inserted in expert compatible substance table 400. In an embodiment, a forms processing module 404 may sort data entered in a submission via graphical user interface 124 by, for instance, sorting data from entries in the graphical user interface 124 to related categories of data; for instance, data entered in an entry relating in the graphical user interface 124 to a compatible substance label 120 may be sorted into variables and/or data structures for storage of compatible substance label 120, while data entered in an entry relating to a category of classified biomarker data and/or an element thereof may be sorted into variables and/or data structures for the storage of, respectively, categories of classified biomarker data or elements of classified biomarker data. Where data is chosen by an expert from pre-selected entries such as drop-down lists, data may be stored directly; where data is entered in textual form, language processing module 128 may be used to map data to an appropriate existing label, for instance using a vector similarity test or other synonym-sensitive language processing test to map classified biometric data to an existing label. Alternatively or additionally, when a language processing algorithm, such as vector similarity comparison, indicates that an entry is not a synonym of an existing label, language processing module 128 may indicate that entry should be treated as relating to a new label; this may be determined by, e.g., comparison to a threshold number of cosine similarity and/or other geometric measures of vector similarity of the entered text to a nearest existent label, and determination that a degree of similarity falls below the threshold number and/or a degree of dissimilarity falls above the threshold number. Data from expert textual submissions 408, such as accomplished by filling out a paper or PDF form and/or submitting narrative information, may likewise be processed using language processing module 128 114. Data may be extracted from expert papers 412, which may include without limitation publications in medical and/or scientific journals, by language processing module 128 114 via any suitable process as described herein. Persons skilled in the art, upon reviewing the entirety of this disclosure, will be aware of various additional methods whereby novel terms may be separated from already-classified terms and/or synonyms therefore, as consistent with this disclosure. Expert compatible substance table 400 may include a single table and/or a plurality of tables; plurality of tables may include tables for particular categories of compatible substance label 120 such as an epigenetic table, a gut wall table, a microbiome table, a nutrient table, a genetic table, and a metabolic table (not shown), to name a few non-limiting examples presented for illustrative purposes only.

With continued reference to FIG. 4, one or more database tables in expert knowledge database 204 may include, an expert dimension table 416 may list one or more body dimensions as described by experts, and one or more biomarkers associated with one or more body dimensions. As a further example an expert biomarker table 420 may list one or more biomarkers as described and input by experts and associated dimensions that biomarkers may be classified into. As an additional example, an expert biomarker extraction table 424 may include information pertaining to biological extraction and/or medical test or collection necessary to obtain a particular biomarker, such as for example a tissue sample that may include a urine sample, blood sample, hair sample, cerebrospinal fluid sample, buccal sample, sputum sample, and the like. Tables presented above are presented for exemplary purposes only; persons skilled in the art will be aware of various ways in which data may be organized in expert knowledge database 204 consistently with this disclosure Referring now to FIG. 5, an exemplary embodiment of a compatible substance label 120 database 212 is illustrated. Compatible substance database 212 may, as a non-limiting example, organize data stored in the compatible substance database 212 according to one or more database tables. One or more database tables may be linked to one another by, for instance, common column values. For instance, a common column between two tables of compatible substance database 212 may include an identifier of an expert submission, such as a form entry, textual submission, expert paper, or the like, for instance as defined below; as a result, a query may be able to retrieve all rows from any table pertaining to a given submission or set thereof. Other columns may include any other category usable for organization or subdivision of expert data, including types of expert data, names and/or identifiers of experts submitting the data, times of submission, or the like; persons skilled in the art, upon reviewing the entirety of this disclosure, will be aware of various ways in which expert data from one or more tables may be linked and/or related to expert data in one or more other tables.

Figure 5:
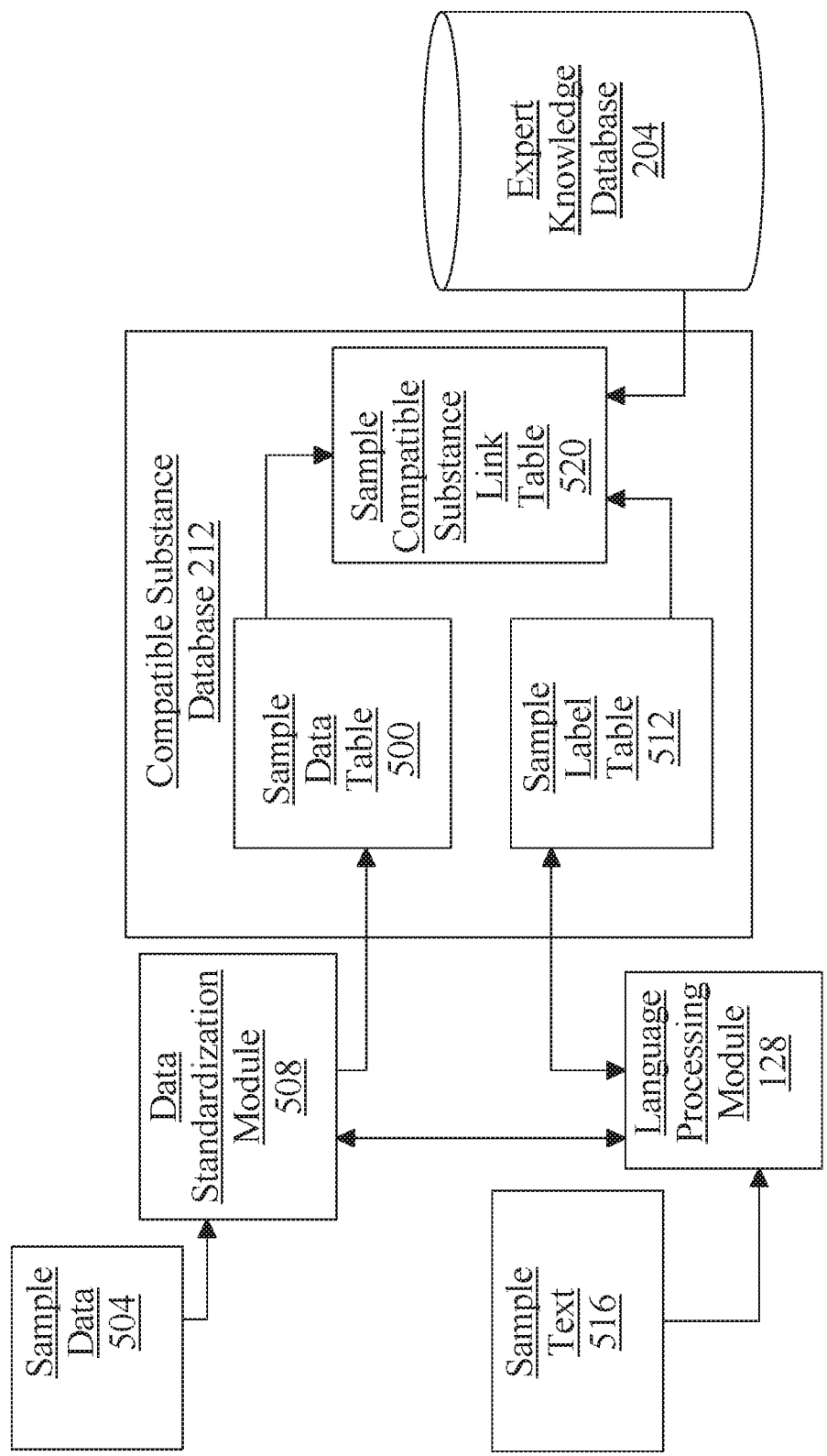
FIG. 5 is a block diagram illustrating an exemplary embodiment of a compatible substance database.

Still referring to FIG. 5, one or more database tables in compatible substance database 212 may include, as a non-limiting example, a sample data table 500. Sample data table 500 may be a table listing sample data, along with, for instance, one or more linking columns to link such data to other information stored in compatible substance database 212. In an embodiment, sample data 504 may be acquired, for instance from classified biomarker database 200, in a raw or unsorted form, and may be translated into standard forms, such as standard units of measurement, labels associated with particular physiological data values, or the like; this may be accomplished using a data standardization module 508, which may perform unit conversions. Data standardization module 508 may alternatively or additionally map textual information, such as labels describing values tested for or the like, using language processing module 128 or equivalent components and/or algorithms thereto.

Continuing to refer to FIG. 5, compatible substance database 212 may include a sample label table 512; sample label table 512 may list compatible substance label 120 received with and/or extracted from physiological samples, for instance as received in the form of sample text 516. A language processing module 128 may compare textual information so received to compatible substance labels and/or form new compatible substance label 120 according to any suitable process as described above. Sample compatible substance link table may combine samples with compatible substance label 120, as acquired from sample label table and/or expert knowledge database 204; combination may be performed by listing together in rows or by relating indices or common columns of two or more tables to each other. Tables presented above are presented for exemplary purposes only; persons skilled in the art will be aware of various ways in which data may be organized in expert knowledge database 204 consistently with this disclosure.

Figure 6:
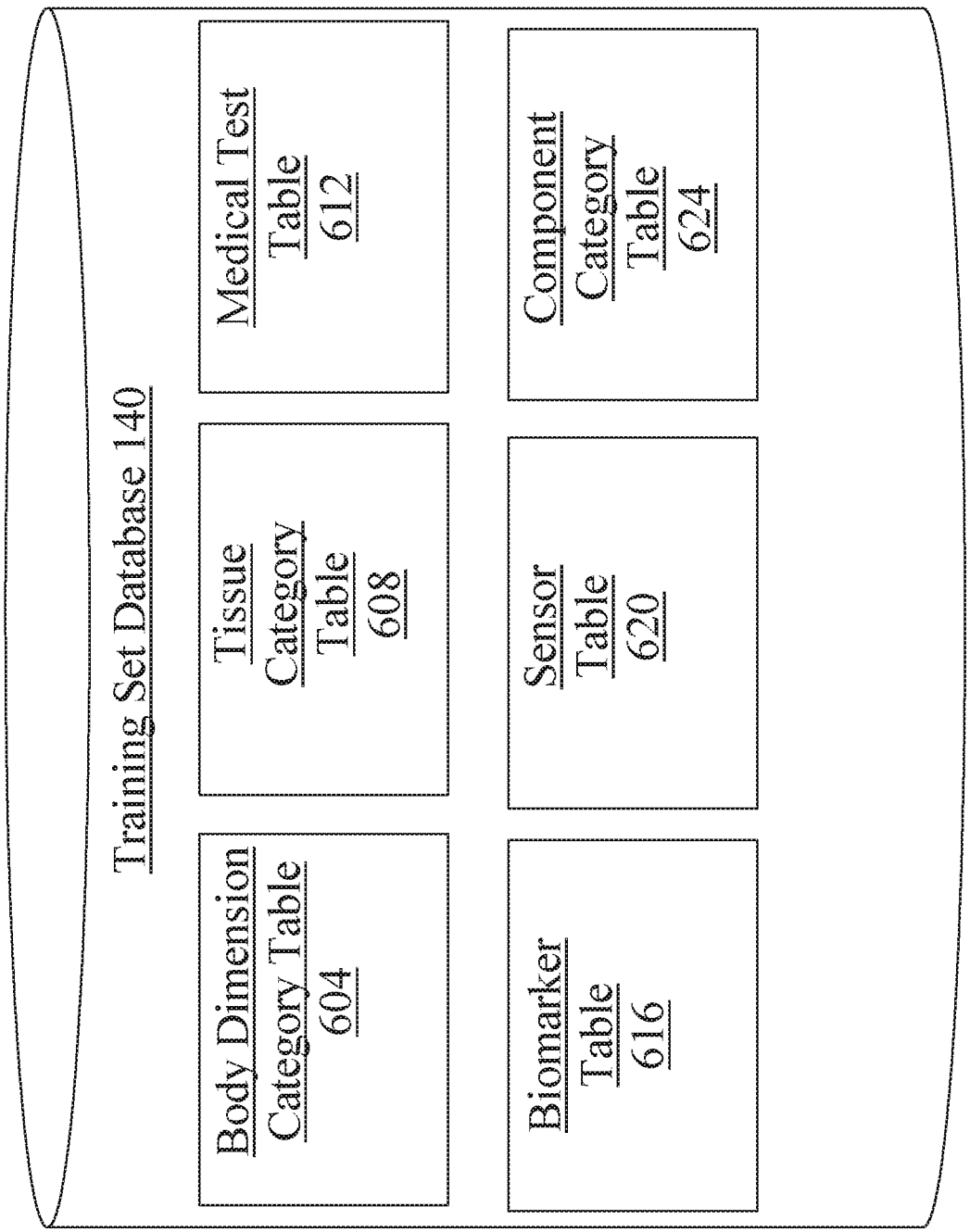
FIG. 6 is a block diagram illustrating an exemplary embodiment of a training set database.

Referring now to FIG. 6, an exemplary embodiment of training set database 140 is illustrated which may be implemented in any manner suitable for implementation of classified biomarker database 200. Training set database 140 may contain training sets pertaining to different categories and classifications of information, including training set components which may contain sub-categories of different training sets. One or more database tables contained within training set database 140 table 600 may include without limitation body dimension category table 604; body dimension category table 604 may contain training sets pertaining to different body dimensions correlated to compatible substance label 120. Body dimensions may include for example, epigenetic, gut wall, microbiome, nutrient, genetic, and metabolic and correlated to compatible substance label 120. One or more database tables contained within training set database 140 table 600 may include without limitation tissue category table 608; tissue category table 608 may contain training sets pertaining to different tissue samples that may be analyzed for biomarkers which may be correlated to compatible substance label 120. Tissue may include for example blood, cerebrospinal fluid, urine, blood plasma, synovial fluid, amniotic fluid, lymph, tears, saliva, semen, aqueous humor, vaginal lubrication, bile, mucus, vitreous body, gastric acid, which may be correlated to compatible substance label 120. One or more database tables contained within training set database 140 table 600 may include without limitation medical test table 612; medical test table 612 may contain training sets containing medical tests and medical test results correlated to compatible substance label 120. Medical tests may include any medical test, medical procedure, and/or medical test or procedure results that may be utilized to obtain biomarkers and tissue samples such as for example, an endoscopy procedure utilized to collect a liver tissue sample, or a blood draw collected and analyzed for circulating hormone levels. One or more database tables contained within training set database 140 may include without limitation sensor table 620; sensor table 620 may contain training sets containing sensor data correlated to compatible substance label 120. Sensor data may include any biomarker data that may be obtained from a sensor such as for example, a wearable device that detects a user's sleeping habits or a heart rate monitor contained within a watch. One or more database tables contained within training set database 140 table 600 may include without limitation component category table 624; component category table 624 may contain components or sub-categories of training sets including any of the training sets as described herein. For example, tissue training sets may be broken down in sub-categories such as for example blood tests correlated to compatible substance label 120 and urine tests correlate to compatible substance label 120. Sub-categories may be broken down into further sub-categories such as blood tests that may be further categorized into complete blood count correlated to compatible substance label 120, prothrombin time correlated to compatible substance label 120, metabolic panel correlated to compatible substance label 120, lipid panel correlated to compatible substance label 120, liver panel correlated to compatible substance label 120 and the like. In an embodiment, training sets and/or components of training sets may be categorized and contained within more than one database tables contained within training set database 140 table 600. For instance and without limitation, a training set such as blood glucose test correlated to compatible substance label 120 may be contained within tissue category table 608 and component category table 624. In yet another non-limiting example, a training set such as heart rate correlated to compatible substance label 120 may be categorized and contained within one or more database tables contained within training set database 140 table 600 including for example medical test table 612 and sensor table 620. Tables presented above are presented for exemplary purposes only; persons skilled in the art will be aware of various ways in which data may be organized in training set database 140 consistently with this disclosure.

Figure 7:
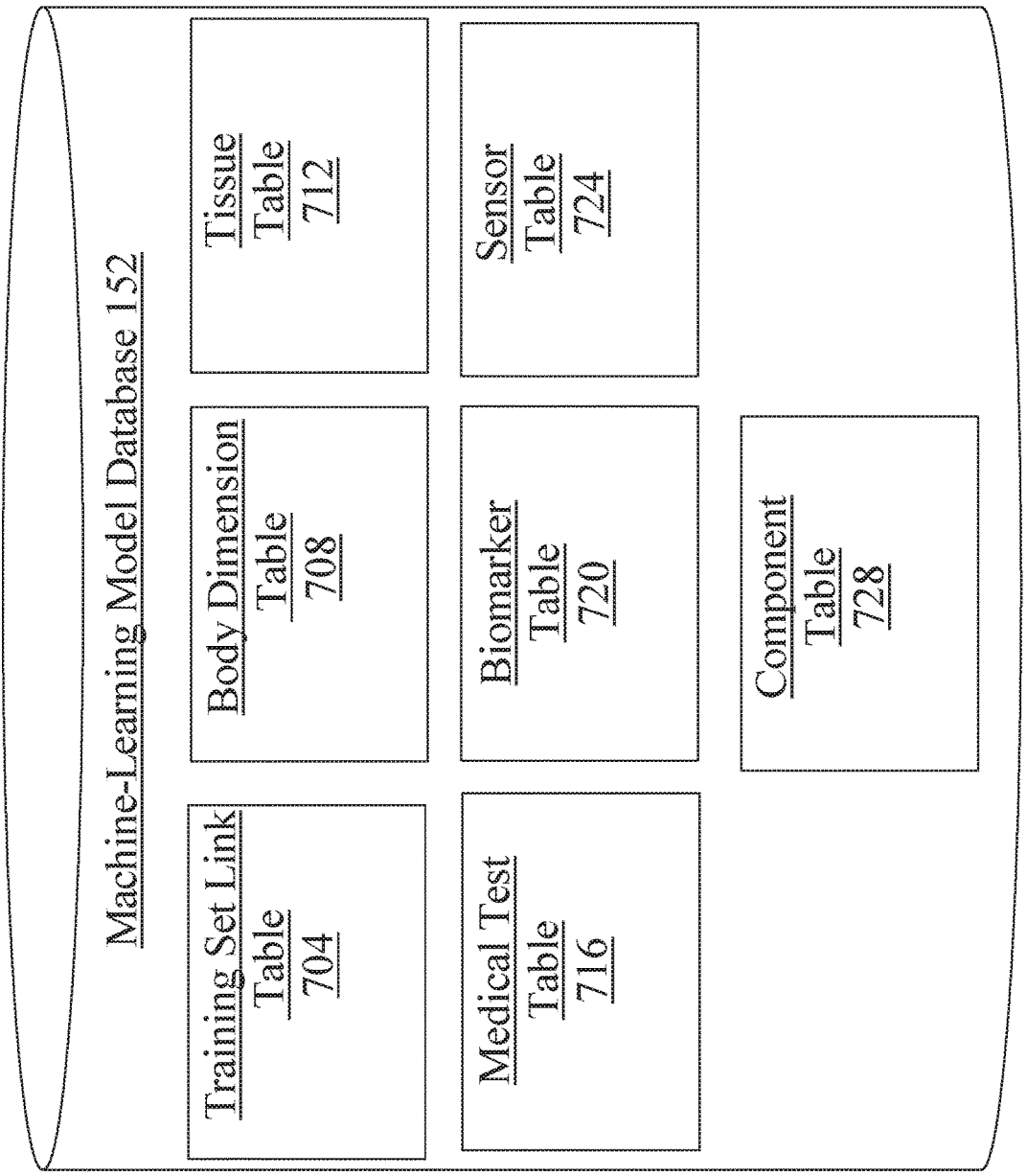
FIG. 7 is a block diagram illustrating an exemplary embodiment of a machine-learning model database.

Referring now to FIG. 7, an exemplary embodiment of machine-learning model database 152 is illustrated which may be implemented in any manner suitable for implementation of classified biomarker database 200. Machine-learning model database 152 may contain machine-learning models categorized and linked to training sets. Machine-learning models may include any of the machine-learning models as described herein. One or more database tables contained within machine-learning model database 152 may include training set link table 704; training set link table 704 may list training sets received with and/or correlated with machine-learning models. Training set link table may combine training sets with machine-learning models, as acquired from expert knowledge database for instance; combination may be performed by listing together in rows or by common columns of two or more tables to each other. One or more database tables contained within machine-learning model database 152 may include body dimension category table; body dimension category table may include machine-learning models correlated to body dimension data, including any of the body dimensions as described herein, including for example epigenetic, gut wall, microbiome, nutrient, genetic, and metabolic. One or more database tables contained within machine-learning model database 152 704 may include tissue category table 712; tissue category table 712 may include machine-learning models correlated to tissue sample data, including any of the tissue samples as described herein. One or more database tables contained within machine-learning model database 152 may include medical test table 716; medical test table 716 may include machine-learning models correlated to medical test data, including any of the medical tests as described herein. One or more database tables contained within machine-learning model database 152 may include biomarker table 720; biomarker table 720 may include machine-learning models correlated to biomarker data, including any of the biomarkers as described herein. One or more database tables contained within machine-learning model database 152 may include sensor table 724; sensor table 724 may include machine-learning models correlated to sensor data, including any of the sensor data as described herein. One or more database tables contained within machine-learning model database 152 may include component table 728; component table 728 may include machine-learning models correlated to training data component data; including any of the training data components as described herein. Tables presented above are presented for exemplary purposes only; persons skilled in the art will be aware of various ways in which data may be organized in machine-learning model database 152 consistently with this disclosure.

Figure 8:
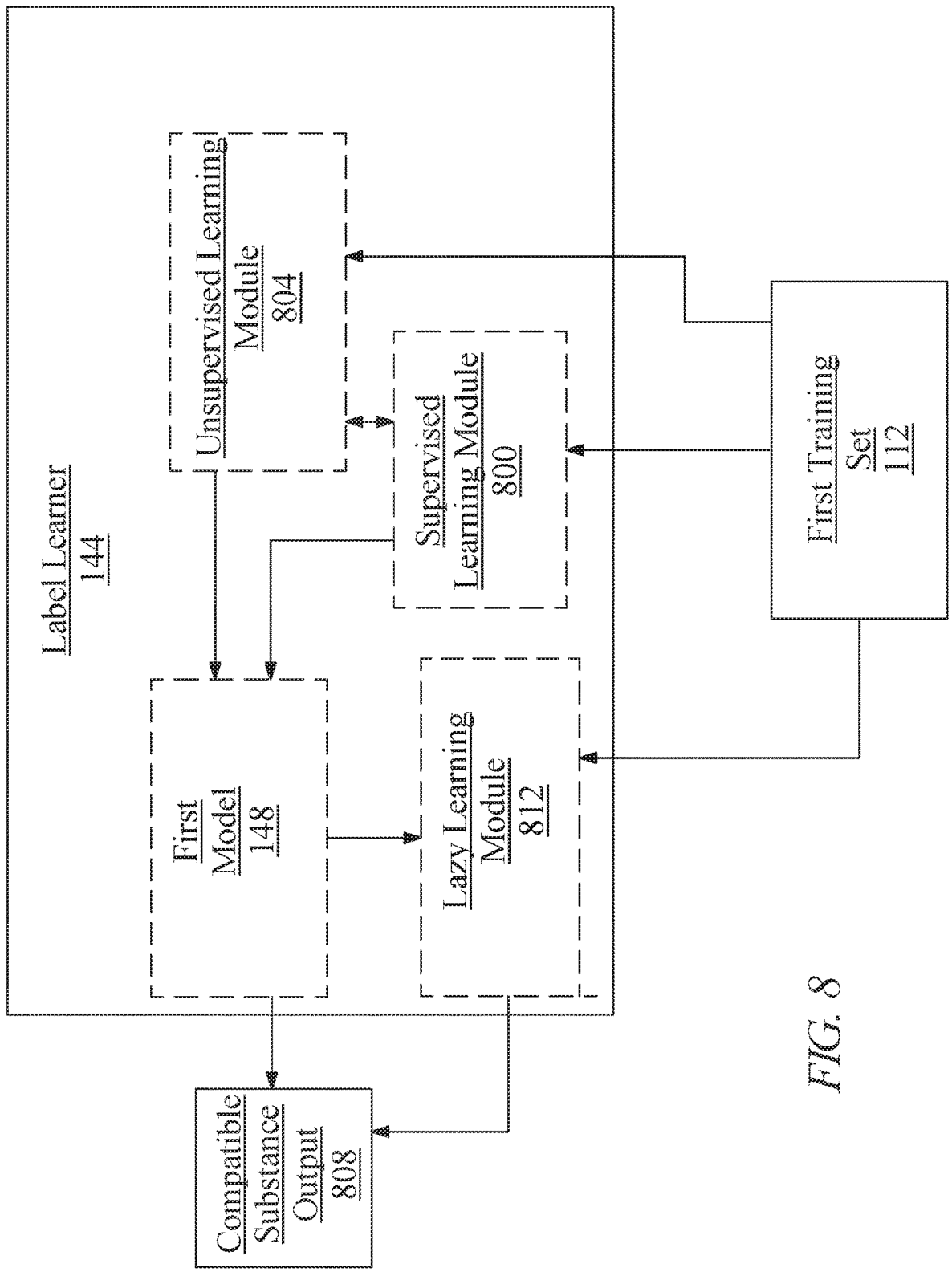
FIG. 8 is a block diagram illustrating an exemplary embodiment of a label learner and associated system elements.

Referring now to FIG. 8, an exemplary embodiment of at least a label learner 144 is illustrated. Machine-learning algorithms used by at least a label learner 144 may include supervised machine-learning algorithms, which may, as a non-limiting example be executed using a supervised learning module 800 executing on at least a server 104 and/or on another computing device in communication with at least a server 104, which may include any hardware or software module. Supervised machine learning algorithms, as defined herein, include algorithms that receive a training set relating a number of inputs to a number of outputs, and seek to find one or more mathematical relations relating inputs to outputs, where each of the one or more mathematical relations is optimal according to some criterion specified to the algorithm using some scoring function. For instance, a supervised learning algorithm may use elements of classified biomarker data as inputs, compatible substance label 120 as outputs, and a scoring function representing a desired form of relationship to be detected between elements of classified biomarker data and compatible substance label 120; scoring function may, for instance, seek to maximize the probability that a given element of classified biomarker data and/or combination of elements of classified biomarker data is associated with a given compatible substance label 120 and/or combination of compatible substance label 120 to minimize the probability that a given element of classified biomarker data and/or combination of elements of classified biomarker data is not associated with a given compatible substance label 120 and/or combination of compatible substance label 120. In yet another non-limiting example, a supervised learning algorithm may use elements of tissue data as inputs, compatible substance label 120 as outputs, and a scoring function representing a desired form of relationship to be detected between elements of tissue data and compatible substance label 120. In yet another non-limiting example, a supervised learning algorithm may use elements of medical test data as inputs, compatible substance label 120 as outputs, and a scoring function representing a desired form of relationship to be detected between elements of medical test data and compatible substance label 120. In yet another non-limiting example, a supervised learning algorithm may use elements of sensor data as inputs, compatible substance label 120 as outputs, and a scoring function representing a desired form of relationship to be detected between elements of sensor data and compatible substance label 120. In yet another non-limiting example, a supervised learning algorithm may use elements of component categories of training data as inputs, compatible substance label 120 as outputs, and a scoring function representing a desired form of relationship to be detected between elements of training data components and compatible substance label 120. Scoring function may be expressed as a risk function representing an "expected loss" of an algorithm relating inputs to outputs, where loss is computed as an error function representing a degree to which a prediction generated by the relation is incorrect when compared to a given input-output pair provided in a training set. Persons skilled in the art, upon reviewing the entirety of this disclosure, will be aware of various possible variations of supervised machine learning algorithms that may be used to determine relation between elements of classified biomarker data and compatible substance label 120. In an embodiment, one or more supervised machine-learning algorithms may be restricted to a particular domain for instance, a supervised machine-learning process may be performed with respect to a given set of parameters and/or categories of parameters that have been suspected to be related to a given set of compatible substance label 120, and/or are specified as linked to a medical specialty and/or field of medicine covering a particular set of compatible substance label 120. As a non-limiting example, a particular set of blood test biomarkers and/or sensor data may be typically used to recommend certain compatible substances, and a supervised machine-learning process may be performed to relate those blood test biomarkers and/or sensor data to the various compatible substances; in an embodiment, domain restrictions of supervised machine-learning procedures may improve accuracy of resulting models by ignoring artifacts in training data. Domain restrictions may be suggested by experts and/or deduced from known purposes for particular evaluations and/or known tests used to evaluate compatible substance label 120. Additional supervised learning processes may be performed without domain restrictions to detect, for instance, previously unknown and/or unsuspected relationships between classified biomarker data and compatible substance label 120.

With continued reference to FIG. 8, machine-learning algorithms may include unsupervised processes; unsupervised processes may, as a non-limiting example, be executed by an unsupervised learning module 804 executing on at least a server 104 and/or on another computing device in communication with at least a server 104, which may include any hardware or software module. An unsupervised machine-learning process, as used herein, is a process that derives inferences in datasets without regard to labels; as a result, an unsupervised machine-learning process may be free to discover any structure, relationship, and/or correlation provided in the data. For instance, and without limitation, at least a label learner 144 and/or at least a server 104 may perform an unsupervised machine learning process on first training set 112, which may cluster data of first training set 112 according to detected relationships between elements of the first training set 112, including without limitation correlations of elements of classified biomarker data to each other and correlations of compatible substance label 120 to each other; such relations may then be combined with supervised machine learning results to add new criteria for at least a label learner 144 to apply in relating classified biomarker data to compatible substance label 120. As a non-limiting, illustrative example, an unsupervised process may determine that a first element of classified biomarker data acquired in a blood test correlates closely with a second element of user classified biomarker data, where the first element has been linked via supervised learning processes to a given compatible substance label 120, but the second has not; for instance, the second element may not have been defined as an input for the supervised learning process, or may pertain to a domain outside of a domain limitation for the supervised learning process. Continuing the example a close correlation between first element of classified biomarker data and second element of classified biomarker data may indicate that the second element is also a good predictor for the compatible substance label 120; second element may be included in a new supervised process to derive a relationship or may be used as a synonym or proxy for the first classified biomarker data 116 element by at least a label learner 144.

Still referring to FIG. 8, at least a server 104 and/or at least a label learner 144 may detect further significant categories of classified biomarker data, relationships of such categories to compatible substance label 120, and/or categories of compatible substance label 120 using machine-learning processes, including without limitation unsupervised machine-learning processes as described above; such newly identified categories, as well as categories entered by experts in free-form fields as described above, may be added to pre-populated lists of categories, lists used to identify language elements for language processing module 128, and/or lists used to identify and/or score categories detected in documents, as described above. In an embodiment, as additional data is added to system 100, at least a label learner 144 and/or at least a server 104 may continuously or iteratively perform unsupervised machine-learning processes to detect relationships between different elements of the added and/or overall data; in an embodiment, this may enable system 100 to use detected relationships to discover new correlations between biomarkers, body dimensions, tissue data, medical test data, sensor data, training set components and/or compatible substance label 120 and one or more elements of data in large bodies of data, such as genomic, proteomic, and/or microbiome-related data, enabling future supervised learning and/or lazy learning processes as described in further detail below to identify relationships between, e.g., particular clusters of genetic alleles and particular compatible substance label 120 and/or suitable compatible substance label 120. Use of unsupervised learning may greatly enhance the accuracy and detail with which system may detect compatible substance label 120.

With continued reference to FIG. 8, unsupervised processes may be subjected to domain limitations. For instance, and without limitation, an unsupervised process may be performed regarding a comprehensive set of data regarding one person, such as a comprehensive medical history, set of test results, and/or classified biomarker data such as genomic, proteomic, and/or other data concerning that persons. A medical history document may include a case study, such as a case study published in a medical journal or written up by an expert. A medical history document may contain data describing and/or described by a prognosis; for instance, the medical history document may list a diagnosis that a medical practitioner made concerning the patient, a finding that the patient is at risk for a given condition and/or evinces some precursor state for the condition, or the like. A medical history document may contain data describing and/or described by a particular treatment for instance, the medical history document may list a therapy, recommendation, or other treatment process that a medical practitioner described or recommended to a patient. A medical history document may describe an outcome; for instance, medical history document may describe an improvement in a condition describing or described by a prognosis, and/or may describe that the condition did not improve. As another non-limiting example, an unsupervised process may be performed on data concerning a particular cohort of persons; cohort may include, without limitation, a demographic group such as a group of people having a shared age range, ethnic background, nationality, sex, and/or gender. Cohort may include, without limitation, a group of people having a shared value for an element and/or category of classified biomarker data, a group of people having a shared value for an element and/or category of compatible substance label 120; as illustrative examples, cohort could include all people having a certain level or range of levels of blood triglycerides, all people diagnosed with a genetic single nucleotide polymorphism, all people with a SRD5A2 gene mutation, or the like. Persons skilled in the art, upon reviewing the entirety of this disclosure, will be aware of a multiplicity of ways in which cohorts and/or other sets of data may be defined and/or limited for a particular unsupervised learning process.

Still referring to FIG. 8, at least a label learner 144 may alternatively or additionally be designed and configured to generate at least a compatible substance output 807 by executing a lazy learning process as a function of the first training set 112 108 and/or at least a biological extraction; lazy learning processes may be performed by a lazy learning module 812 executing on at least a server 104 and/or on another computing device in communication with at least a server 104, which may include any hardware or software module. A lazy-learning process and/or protocol, which may alternatively be referred to as a "lazy loading" or "call-when-needed" process and/or protocol, may be a process whereby machine learning is conducted upon receipt of an input to be converted to an output, by combining the input and training set to derive the algorithm to be used to produce the output on demand. For instance, an initial set of simulations may be performed to cover a "first guess" at a compatible substance label 120 associated with a user classified biomarker datum, using first training set 112. As a non-limiting example, an initial heuristic may include a ranking of compatible substance label 120 according to relation to a test type of at least a classified biomarker datum, one or more categories of classified biomarker data identified in test type of at least a classified biomarker data, and/or one or more values detected in at least a classified biomarker sample; ranking may include, without limitation, ranking according to significance scores of associations between elements of classified biomarker data and compatible substance label 120, for instance as calculated as described above. Heuristic may include selecting some number of highest-ranking associations and/or compatible substance label 120. At least a label learner 144 may alternatively or additionally implement any suitable "lazy learning" algorithm, including without limitation a K-nearest neighbors algorithm, a lazy naïve Bayes algorithm, or the like; persons skilled in the art, upon reviewing the entirety of this disclosure, will be aware of various lazy-learning algorithms that may be applied to generate compatible substance label 120 as described in this disclosure, including without limitation lazy learning applications of machine-learning algorithms as described in further detail below.

Figure 9:
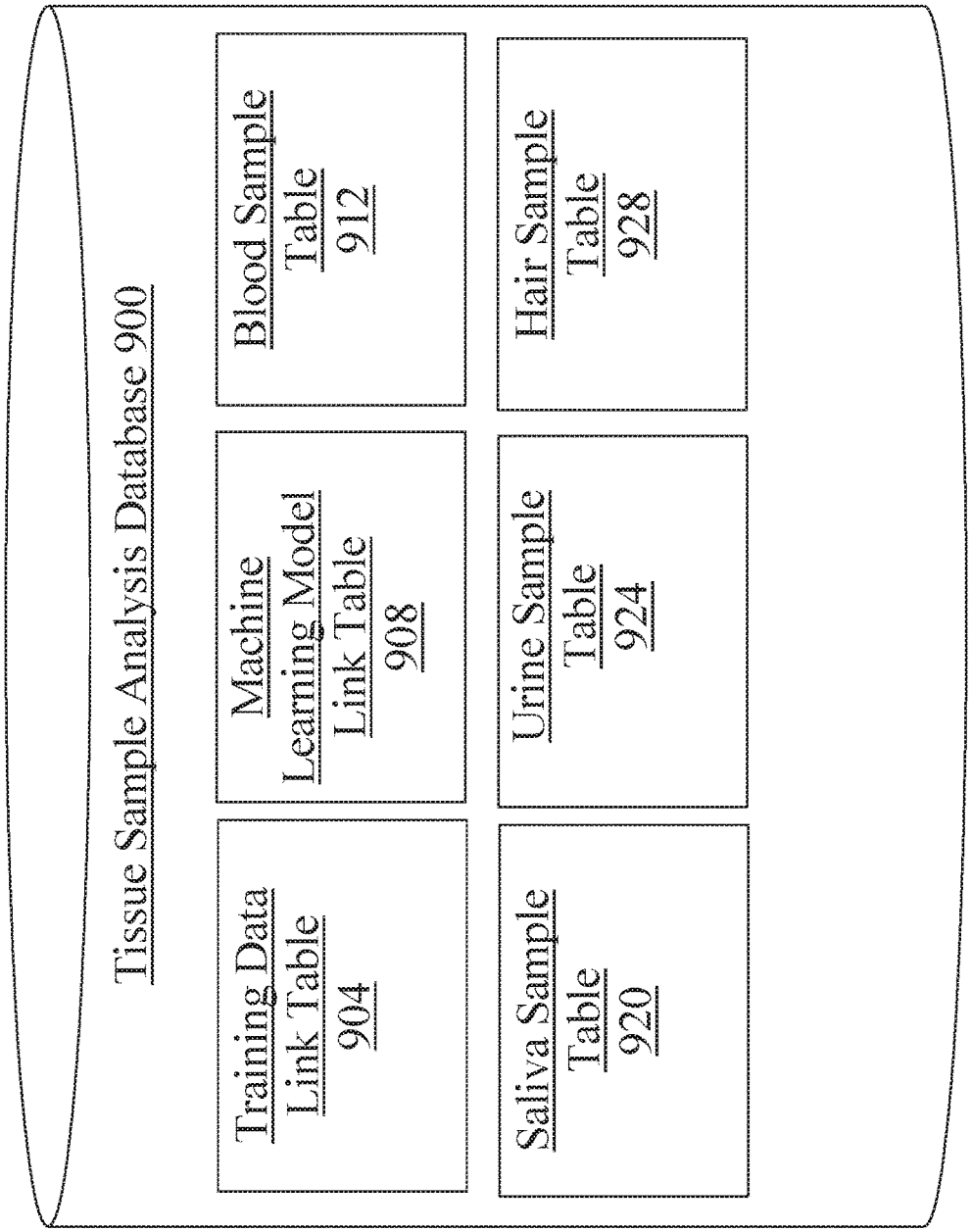
FIG. 9 is a block diagram illustrating an exemplary embodiment of a tissue sample analysis database.

Referring now to FIG. 9, an exemplary embodiment of tissue sample analysis database 900 is illustrated, which may be which may be implemented in any manner suitable for implementation of classified biomarker database 200. Tissue sample analysis database 900 may contain information pertaining to tissue sample analysis and results obtained from tissue sample analysis. Tissue sample analysis table 900 may contain information pertaining to previously recorded tissue samples that may be utilized alone or in combination with biomarker datum to generate compatible element labels. One or more tables contained within tissue sample analysis database 900 may include training data link table 904; training data link table 904 may combine tissue samples with training data sets, as acquired from training set database 140 and expert knowledge database 204. Combination may be performed by listing together in rows or by relating indices or common columns of two or more tables to each other. One or more tables contained within tissue sample analysis database 900 may include machine-learning model link table 908; machine-learning link table 908 may combine tissue samples with machine-learning models, as acquired from machine-learning model database 152 and expert knowledge database 204. Combination may be performed by listing together in rows or by relating indices or common columns of two or more tables to each other. One or more tables contained within tissue sample analysis database 900 may include blood sample table 912; blood sample table 912 may include information describing one or more previous blood samples that a user may have collected and/or had performed. Blood sample may include any kind of blood test or blood analysis such as for example, blood glucose test, calcium blood test, cardiac enzyme test, cholesterol test, c-reactive protein test, serum progesterone level test, serum estradiol level test and the like. One or more database tables contained within tissue sample analysis database 900 may include saliva sample table 920; saliva sample table 920 may include information describing one or more previous saliva samples that a user may have collected and/or had analyzed. Saliva sample may include any kind of salivary test used to detect cortisol levels, hormone levels, gene sequences, gene mutations, heavy metals, iodine levels, and the like. One or more tables contained within tissue sample analysis database 900 may include urine sample table 904; urine sample table 924 may include information describing one or more previous urine samples that a user may have collected and/or had performed. Urine sample may include any kind of urinary test or urinary analysis such as for example to evaluate neurotransmitter levels, iodine levels, heavy metals, hormone levels, ketone levels, absence or presence of bacterial species, absence or presence of fungal species and the like. One or more tables contained within tissue sample analysis database 900 may include hair sample table 928; hair sample table 928 may include information describing one or more previous hair samples that a user may have had analyzed. Hair sample may include any type of hair analysis such as for heavy metal toxicity, bisphenol levels, genetic sequencing, nutrient level evaluation. Other tables contained within tissue sample analysis may include for example, cerebrospinal fluid, blood plasma, synovial fluid, amniotic fluid, lymph, tears, semen, vaginal lubrication, aqueous humor, bile, mucus, vitreous body, gastric acid, muscle biopsy, nervous tissue, epithelial tissue, connective tissue, (not pictured) and the like. Persons skilled in the art, upon reviewing the entirety of this disclosure, will be aware of various forms which may be suitable for use as tissue sample analysis database consistently with this disclosure.

Referring now to FIG. 10, an exemplary embodiment of a compatible substance index value database 156 is illustrated, which may be implemented in any manner suitable for implementation of classified biomarker database 200. Compatible substance index value database 156 may include information describing compatible substance index values for different foods. Compatible substance index value database 156 may be consulted by at least a server 104 when selecting and generating at least a compatible substance instruction set. Compatible substance index value is a value assigned to a compatible substance indicating a degree of compatibility between a first compatible element and a second compatible element for a user with any given biomarker datum. Compatible substance index value may be calculated using any of the methodologies as described above in reference to FIG. 1. Compatible substance index value may contain information allowing for at least a server 104 to select one or more compatible substances as a function of another compatible substance. Compatible substance index value may also allow for at least a server 104 to select compatible substances that may be categorized as belonging to a shared category, such as for example grains or vegetables as described below in more detail in reference to FIG. 11. One or more database tables contained within compatible substance index value database 156 may include alfalfa sprout table 1004; alfalfa sprout table 1004 may include compatible substance index values for alfalfa sprout for any given biomarker datum. For example, alfalfa sprouts may contain a high compatible substance index value for a biomarker that shows low levels of *Streptococcus thermophilus* while alfalfa sprouts may contain a low compatible substance index value for a biomarker that shows high levels of *Lactobacillus lactis*. One or more database tables contained within compatible substance index value database 156 may include hazelnut table 1008; hazelnut table 1008 may include compatible substance index values for hazelnuts for any given biomarker datum. For instance and without limitation, hazelnut may have a high compatible substance index value for a biomarker that shows low gastrointestinal levels of *Streptococcus* and *Lactobacillus* but may have a low compatible substance index value for a biomarker that shows high blood levels of mold. One or more database tables contained within compatible substance index value database 156 may include green tea table 1012; green tea table 1012 may include compatible substance index values for green tea for any given biomarker datum. For example, green tea may contain a high compatible substance index value for a user who is a high metabolizer of the CYP1A2 gene while green tea may contain a low compatible substance index value for a user who is a slow metabolizer of the CYP1A2 gene. One or more database tables contained within compatible substance index value database 156 may include lamb table 1016; lamb table 1016 may include compatible substance index values for lamb for any given biomarker datum. For example, lamb may have a high compatible substance index value for a biomarker such as a nutrient test showing low blood levels of l-carnitine, while lamb may have a moderate compatible substance index value for a biomarker such as a nutrient test showing normal blood levels of l-carnitine. One or more database tables contained within compatible substance index value database 156 may include Munster cheese table 1020; Munster cheese table 1020 may include compatible substance index values for Munster Cheese for any given biomarker datum. For example, Munster cheese may contain a high compatible substance index value for a user who does not have a mutation of the LCT 2q21 gene that controls lactase production, while Munster cheese may contain a low compatible substance index value for a user who does have a mutation of the LCT 2q21 gene and is unable to produce lactase. One or more database tables contained within compatible substance index value database 156 may include raspberry table 1024, raspberry table 1024 may include compatible substance index values for raspberries for any given biomarker datum. For example, raspberry may contain a low compatible substance index value for a biomarker showing presence of raspberry bushy dwarf virus in a user's gastrointestinal system, while raspberry may contain a high compatible substance index value for a biomarker showing APOE4 gene mutation that recommends blueberries, which may have a high compatible substance index value to be substituted instead for raspberries or recommended together in conjunction with blueberries for a user with the APOE4 gene mutation. Tables contained within compatible substance index value database 156 may include other foods including for example, chestnuts, coffee, cantaloupe melon, pistachios, arugula, bamboo shoots, beet greens, broccoli, burdock root, artichoke, asparagus, beet, bok choy, Brussel sprouts, cabbage, celery (not picture). Persons skilled in the art upon reviewing the entirety of this disclosure, will be aware of various forms which may be suitable for use as compatible substance index value database 156 consistently with this disclosure.

Figure 11:
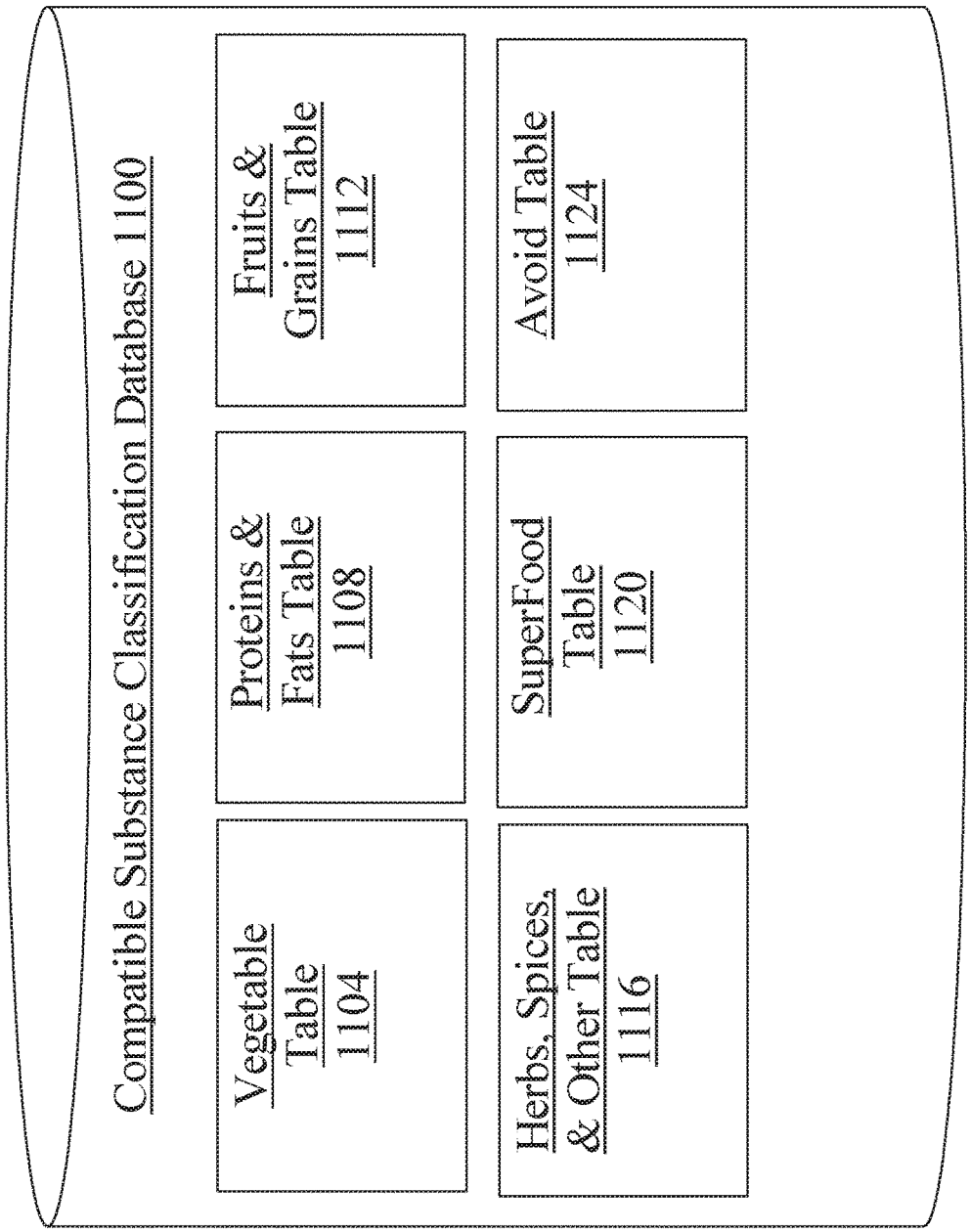
FIG. 11 is a block diagram illustrating an exemplary embodiment of a compatible substance classification database.

Referring now to FIG. 11, an exemplary embodiment of compatible substance classification database 1100 is illustrated, which may be implemented in any manner suitable for implementation of classified biomarker database 200. Compatible substance classification database 1100 may include information categorizing compatible substances into categories exhibiting shared characteristics. At least a server 104 may consult compatible substance classification database 1100 when generating compatible substance instruction set. In an embodiment, compatible substance instruction set may contain categories that may match categories contained within compatible substance classification database 1100. In an embodiment, at least a server may consult compatible substance classification database 1100 and compatible substance index value database 156 to generate compatible substance instruction set that may contain compatible elements selected based on shared categories contained within compatible substance classification database 1100 and based on compatibility and ability to select a second compatible substance as a function of a first compatible substance based on information contained within compatible substance index value database 156. One or more database tables contained within compatible substance classification database 1100 may include vegetable table 1104; vegetable table 1104 may include all compatible substances classified as vegetables. For example, compatible substances including cauliflower, celery, collard greens, dandelion greens, carrot, cucumber, hard squash, and eggplant may be classified as vegetables. One or more database tables contained within compatible substance classification database 1100 may include proteins and fats table 1108; proteins and fat table 1108 may include all compatible substances classified as proteins and fats. Proteins and fats may include for example, almond milk, avocado oil, grass fed beef, black eyed peas, adzuki beans, anchovy, avocado, black beans bone broth, butter, brazil nuts, chickpeas, chicken, coconut meat, and the like. One or more database tables contained within compatible substance classification database 1100 may include fruits and grains table 1112; fruits and grains table 1112 may include all compatible substances classified as fruits and grains. For example, fruits and grains may include amaranth, apricot, barley, buckwheat, cantaloupe, apple, banana, blackberry, bulgur, cassava, cherry, couscous, currants, dragon fruit, fig, gooseberry, grapes, cranberry, dates, goji berry, grapefruit, huckleberry and the like. One or more database tables contained within compatible substance classification database 1100 may include herbs spices and other table which may include compatible substances classified as herbs, spices, and miscellaneous. Herbs, spices, and other table may include compatible substances such as allspice, bay leaf, cane sugar, caraway seed, celery seed, basil, black pepper, chervil, dill, ginger, honey, cloves, coconut water, herbal tea, horseradish, peppermint, marjoram, molasses, paprika, rosemary and the like. One or more database tables contained within compatible substance classification database 1100 may include superfood table 1120; superfood table 1120 may include all compatible substances classified as superfoods for an individual user. Superfoods may include compatible substances that confer health benefits for a user as a function of a user's biomarker datum. One or more database tables contained within compatible substance classification database 1100 may include avoid table 1124; avoid table 1124 may include compatible substances that do not confer health benefits for a user as a function of a user's biomarker datum and consumption of such compatible substances should be avoided. Persons skilled in the art upon reviewing the entirety of this disclosure, will be aware of various forms which may be suitable for use as compatible substance classification database consistently with this disclosure.

Figure 12:
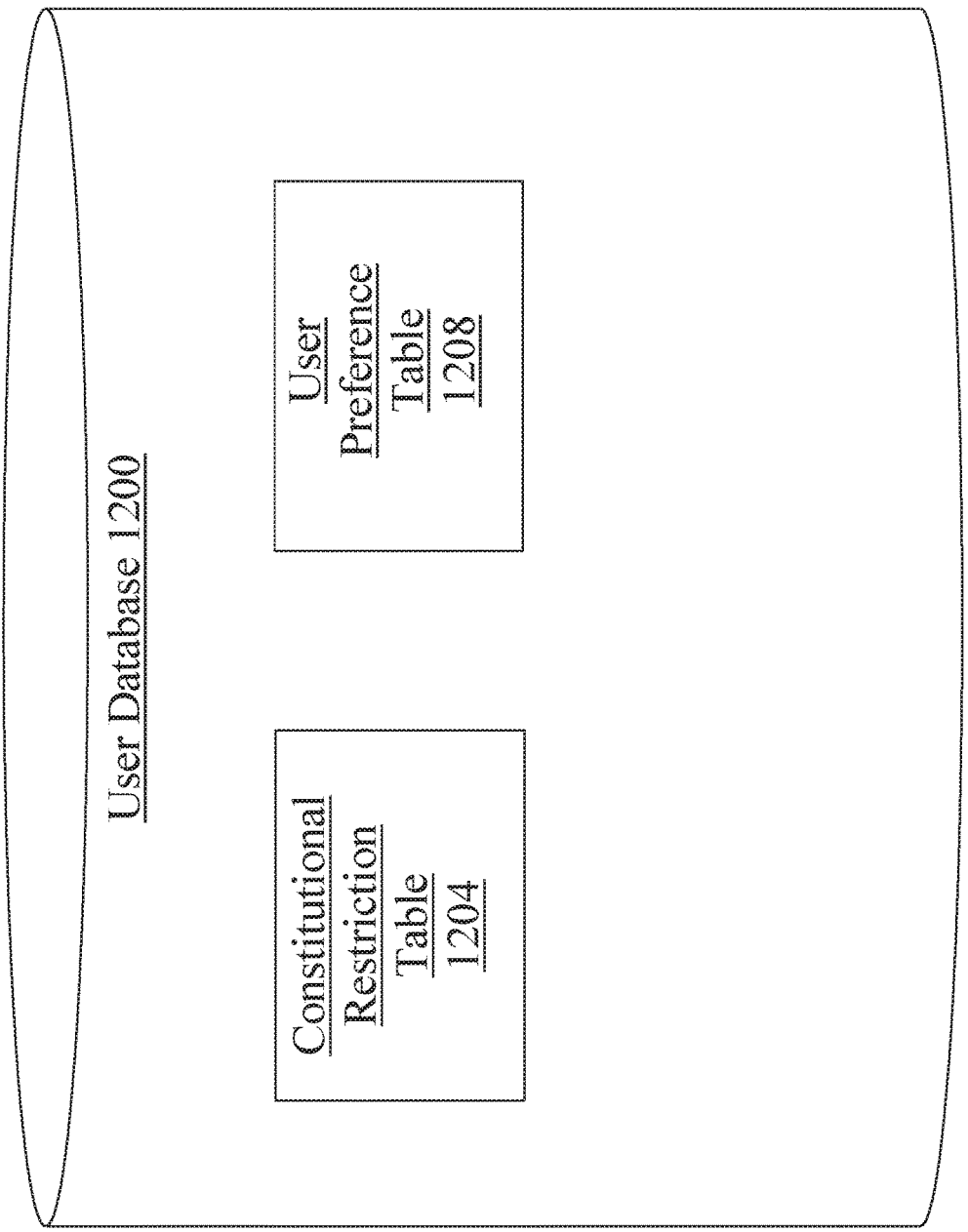
FIG. 12 is a block diagram illustrating an exemplary embodiment of a user database.

Referring now to FIG. 12, an exemplary embodiment of user database 1200 is illustrated, which may be implemented in any manner suitable for implementation of classified biomarker database 200. In an embodiment, at least a server 104 may consult user database 1200 when generating at least a compatible substance instruction set such as for example, when filtering compatible substance recommendations as a function of user preference or user dietary restrictions. One or more database tables in user database 1200 may include, without limitation, a constitution restriction table 1204; at least a constitutional restriction include information pertaining to a user constitutional restriction which may include any compatible substances that a user chooses not to consume for medical or ethical purposes. For instance and without limitation, constitutional restriction table 1204 may contain information such as a user's preference to eat only vegetarian ingredients. In such an instance, a compatible substance instruction set that contains non-vegetarian compatible substances may be filtered by at least a server 104 to remove such compatible substances from compatible substance instruction set. In yet another non-limiting example, constitutional restriction table 1204 may include information such as a user's self-reported nut allergy, whereby all nut containing compatible substances may be filtered off of a compatible substance instruction set for a user with a previously diagnosed nut allergy. One or more database tables in user database 1200 may include, without limitation, a user preference table 1208; at least a user preference may include information describing a user's preference or aversion to specific compatible substances. For example and without limitation, user preference table 1208 may include information describing a user's aversion to eggs or a user's dislike of tomatoes. In an embodiment, user preference table 1208 may include information describing a user's preference or aversion for categories of compatible substances, such as a user's preference for vegetables or a user's aversion to fruits. Persons skilled in the art upon reviewing the entirety of this disclosure, will be aware of various forms which may be suitable for use as user database consistently with this disclosure.

Figure 13:
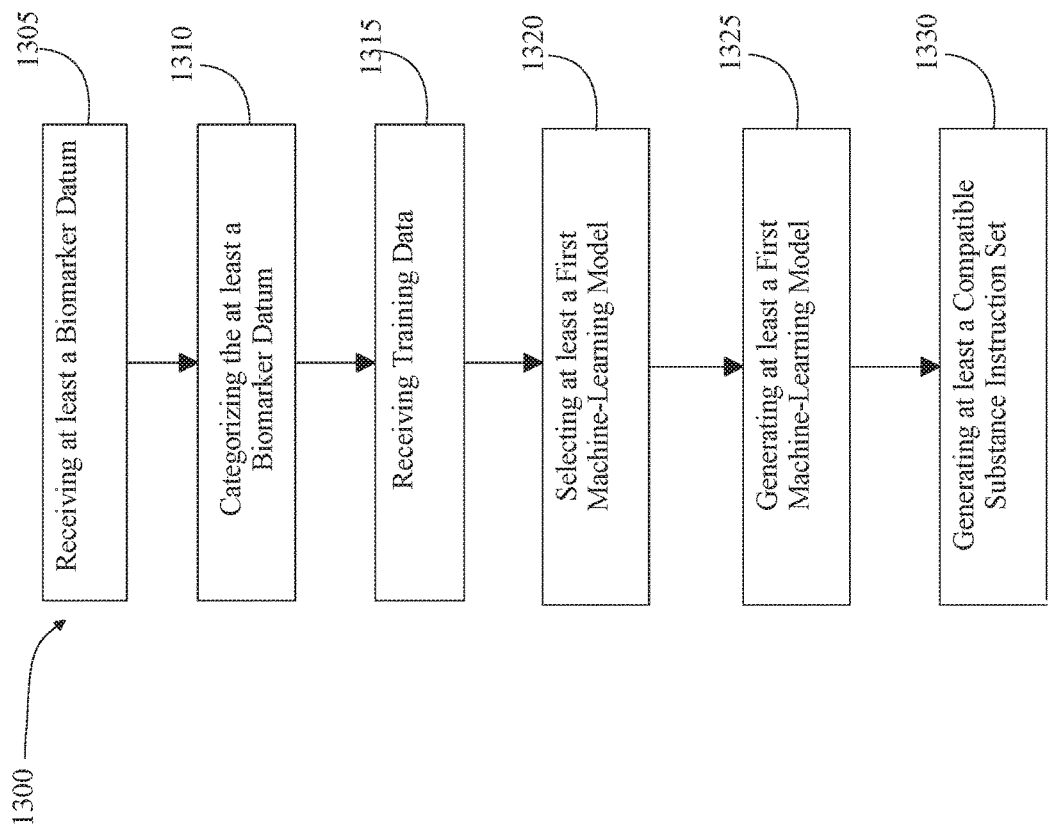
FIG. 13 is a flow diagram illustrating an exemplary embodiment of a method of generating a compatible substance instruction set using artificial intelligence.

Referring now to FIG. 13, an exemplary embodiment of a method of generating a compatible substance instruction set is illustrated. At step 1305, at least a server receives at least a biomarker datum wherein the at least a biomarker datum contains at least an element of body data correlated to at least a body dimension. Biomarker datum includes any element and/or elements of physiological state data. For example and without limitation, biomarker datum may include a DNA methylation analysis of genes such as FHL2, ZNF518B, GNPNAT1, and HLTF. In yet another non-limiting example, biomarker datum may include a hair test analysis of heavy metals such as arsenic, mercury, cadmium, lead, and aluminum. In yet another non-limiting example, at least a biomarker datum may include a salivary measurement of eosinophil protein x (EPX) or a stool test that contains concentration of a specific strain of bacteria. In an embodiment, at least a biomarker datum may include a tissue sample analysis correlated to at least a body dimension. Tissue sample analysis may include a tissue previously analyzed by a laboratory or medical professional such as a medical doctor for examination. In an embodiment, tissue sample analysis may include comparisons of an extracted tissue sample as compared to reference ranges of normal values or normal findings. For instance and without limitation, tissue sample analysis may include a tissue segment taken from the epithelial lining of a user's gastrointestinal tract and analyzed for microbial content as compared to known reference ranges of microbial contents. In an embodiment, element of body data correlated to at least a body dimension may include at least a datum of user test data containing at least a root system label. User test data may include any of the user test data as described above in reference to FIG. 1. Root system label may include any of the root system labels as described above in reference to FIG. 1. User device may include any of the user devices as described herein. At least a biomarker datum may be received using any network and transmission methodology as described herein.

With continued reference to FIG. 13, at step 1310 at least a biomarker datum is categorized as a function of at least a body dimension to produce at least a classified biomarker datum. Biomarker system classification may include classifying biomarker datums having shared characteristics as related to a dimension of the human body. In an embodiment, biomarker system classification may include classifying at least a biomarker datum as a function of a dimension of the human body. Dimension may include epigenetics, gut wall, microbiome, nutrients, genetics, and metabolism. In an embodiment, classification may include comparing at least a biomarker datum to a classified biomarker datum contained within classified biomarker database 200. For instance and without limitation, at least a biomarker datum containing an extracellular blood level of calcium may be compared to a classified extracellular blood level of calcium contained within classified biomarker database 200 that contains a nutrient classification. In such an instance, at least a biomarker datum that matches a classified biomarker datum contained within classified biomarker database 200 may be utilized to classify at least a biomarker datum. In yet another non-limiting example, at least a biomarker datum such as a salivary hormone level may be compared to a classified salivary hormone level contained within classified biomarker database 200. In such an instance, at least a biomarker datum that matches the classified biomarker datum may then be classified accordingly. In yet another non-limiting example, classifying at least a biomarker may include extracting at least a tissue sample result from at least a biomarker datum and retrieving at least a tissue sample classification label from a database. Tissue sample may include any of the tissue samples as described herein. In an embodiment, at least a biomarker may contain or be linked to at least a tissue sample. For instance and without limitation, at least a biomarker may contain tissue samples or tissue samples may be retrieved from a database such as tissue sample analysis database. In an embodiment, at least a biomarker may be classified as a function of retrieving at least a tissue sample from tissue sample analysis database and classifying at least a biomarker as a function of classification of tissue sample. For instance, at least a biomarker containing a blood sample may be classified as a function of classification label given to blood sample contained within tissue sample analysis database. In yet another non-limiting example, at least a biomarker containing a saliva sample may be classified as a function of a classification label given to a saliva sample contained within saliva sample table located within tissue sample analysis database 900. In an embodiment, at least a biomarker datum may be classified as a function of language processing module 128. For instance and without limitation, language processing module 128 may extract keywords or text that may accompany at least a biomarker datum. In such an instance, language processing module 128 may extract keywords or trigger words relating to dimensions of the body and utilize such keywords or trigger words to classify the at least a biomarker datum. For instance and without limitation, at least a biomarker datum containing a keyword such as "bacterial strain" and "leaky gut" may be utilized to classify the least a biomarker datum as pertaining to gut wall dimension of body as a function of keywords extracted by language processing module 128. In such an instance, key words extracted by language processing module 128 may be stored within a database, such as for example tissue sample analysis database 900 or classified biomarker database 200.

With continued reference to FIG. 13, at step 1315 at least a server receives training data. Training data may include any of the training data as described herein. In an embodiment, receiving training data includes receiving a first training set 112 including a plurality of first data entries, each first data entry of the plurality of first data entries including at least a first element of first classified biomarker data 116 and at least a correlated compatible substance label 120. First classified biomarker data 116 may include biomarker data that has been classified to a dimension of the body. For instance and without limitation, biomarker data such as aerobic bacterial cultures, anerobic bacterial cultures, beta-glucuronidase, stool pH, barium enema test results, and stool fat triglyceride levels may be classified as belonging to dimension of the body pertaining to gut wall. In yet another non-limiting example, biomarker data such as extracellular levels of Vitamin A, Vitamin B1, and Vitamin E, and intracellular red blood cell levels of Vitamin D, Vitamin K2, and folate may be classified as belonging to dimension of the body pertaining to nutrients. In an embodiment, biomarker datums may be classified to more than one dimension of the body. For instance and without limitation, biomarker datum such as stool examination for *Barnesiella* species may be classified as belonging to gut wall dimension and microbiome dimension. In yet another non-limiting example, biomarker datum such as BCMO1 gene that produces enzymes that metabolize and activate Vitamin A may be classified as belonging to genetic dimension and nutrient dimension. Correlated compatible substance label 120 may include any of the correlated compatible substance label 120 as described herein. Compatible substance label 120 may be correlated to at least a classified biomarker data using any of the correlations as described herein, including receiving correlations from experts such as from expert knowledge database. Receiving training data may include receiving at least a first element of classified biomarker datum from at least a constitutional analysis. Constitutional analysis may include any of the constitutional analysis as described above in reference to FIG. 1013. Receiving training data may include receiving at least a first element of classified biomarker datum from at least a tissue sample. Tissue sample may include any of the tissue samples as described above in reference to FIGS. 1-13.

With continued reference to FIG. 13, receiving training data may include receiving a second training set 132. Second training set 132 may include a plurality of second data entries, each second data entry of the plurality of second data entries including at least a second element of second classified biomarker data 136 and at least a correlated compatible substance label 120. Second classified biomarker data 136 may include any biomarker data that has been classified to a second dimension of the body that may be different than the first classified biomarker data 116 received in first training set 112. In an embodiment, at least a server may be configured to receive a plurality of training sets. In an embodiment, receiving a training set may including retrieving a training set from a database, such as for example training set database 140. In an embodiment, receiving a training set may include receiving a component of a training set, such as for example, a sub-set of training data contained within a body dimension training set.

With continued reference to FIG. 13, at step 1320 at least a server selects at least a first machine-learning model 148 as a function of the first training set 112 and the at least a biomarker datum. Selecting at least a machine-learning model may include selecting at least a machine-learning model from machine-learning model database 152. In an embodiment, at least a server 104 may select at least a machine-learning algorithm as a function of the first training set 112. Machine-learning model database 152 may contain information linking machine-learning algorithms to training sets, such as those contained within training set database 140. For instance and without limitation, a training set selected from training set database 140 may be selected and linked to a machine-learning model such as k-nearest neighbor algorithm within machine-learning model database 152. In yet another non-limiting example, a training set selected from training set database 140 may be selected and linked to an unsupervised machine-learning process within machine-learning model database 152. In an embodiment, machine-learning models contained within machine-learning model database 152 may be categorized according to different categories of training sets. For instance, a training set relating body dimension categories to compatible substance label 120 may contain information pertaining to machine-learning algorithms to select for those particular training sets within machine-learning model database 152. In an embodiment, at least a machine-learning model may be selected as a function of the at least a categorized biomarker datum. For instance and without limitation, at least a biomarker datum that is classified as belonging to gut wall body dimension, may be utilized to select at least a machine-learning model that relates to gut wall dimension from machine-learning model database 152 such as by consulting body dimension table 708. In yet another non-limiting example, at least a biomarker datum that is classified as belonging to epigenetic body dimension may be utilized to select at least a machine-learning model that relates to epigenetic body dimension from machine-learning model database 152 such as by consulting body dimension table 708. In an embodiment, body dimension table 708 may be further broken down into categories of body dimensions including for example, epigenetic, gut wall, microbiome, nutrient, genetic, and metabolic. In an embodiment, at least a biomarker may be utilized to select at least a machine-learning algorithm. For instance and without limitation, at least a biomarker may be utilized to select at least a machine-learning model that relates to the at least a biomarker from machine-learning model database 152 such as by consulting information contained within biomarker table 720. In an embodiment, selecting at least a first machine-learning model may include retrieving at least a first machine-learning model from a database as a function of the at least a first element of first classified biomarker datum contained within the first training set.

With continued reference to FIG. 13, at step 1325 at least a server generates at least a first machine-learning model using the first training set wherein the first machine-learning model outputs at least a compatible substance containing at least a compatible substance index value as a function of relating the at least a user biomarker datum to at least a compatible substance using the first training set and the at least a first machine-learning model. Machine-learning models may include any of the machine-learning models as described above in reference to FIGS. 1-13. In an embodiment, this may include generating several machine-learning models. For instance and without limitation, a plurality of biomarkers may be utilized to select several machine-learning models. For example, each biomarker of plurality of biomarkers may select a plurality of machine-learning algorithms that may be utilized to generate at least a compatible substance instruction set. For instance and without limitation, at least a biomarker that contains a blood sample, a urine analysis, and a microbiome sequence may each be utilized to select at least a machine-learning model to generate at least a compatible substance instruction set. In yet another non-limiting example, at least a server may generate an unsupervised machine-learning model followed by a supervised machine-learning model which may include any of the models as described above. In yet another non-limiting example, at least a server may generate an unsupervised machine-learning algorithm followed by a neural network model. This may include any of the machine-learning models as described above in reference to FIGS. 1-13.

With continued reference to FIG. 13, at step 1330 at least a server generates at least a compatible substance instruction set containing at least a compatible substance ranked as a function of the at least a compatible substance index value. Generating compatible substance instruction set may include retrieving at least a compatible substance index value from a database and generating at least a compatible substance instruction set as a function of the at least a compatible substance index value. Compatible substance index value may include any of the compatible substance index values as described above in reference to FIG. 1 and FIG. 10. In an embodiment, at least a compatible substance may be selected and included within compatible substance instruction set as a function of compatible substance index value. For example, a compatible substance containing a high compatible substance index value for a given user's biomarker may be selected and included within compatible substance instruction set. In yet another non-limiting example, a compatible substance containing a low compatible substance index value for a given user's biomarker may not be selected and included within compatible substance instruction set. In an embodiment, a first compatible substance may be selected as a function of a first compatible substance index value and a second compatible substance may be selected as a function of the first compatible substance index value and a second compatible substance index value. For instance and without limitation, a compatible substance index value may provide information as to whether a second compatible substance may be selected as a function of a first compatible substance. For example, a compatible substance index value for blueberries may be utilized and compared to a compatible substance index values for raspberries to determine whether raspberries may be selected and recommended to a user as a function of recommending blueberries to a user. In an embodiment, compatible substance index value may be utilized to generate recommendations based on classifications of compatible substances, such as the classification scheme described above in reference to FIG. 11. For instance, a compatible substance index value for a vegetable such as kale may be utilized and compared to compatible substance index value for a vegetable such as collard greens to determine whether collard greens can be recommended as a function of recommending kale. Compatible substance index value may be evaluated as a function of at least a biomarker datum received from a user client device 108 128. For instance and without limitation, compatible substance index value may be linked to a user biomarker datum. For example, a first user with a biomarker for a urinary test of bacteria may be linked to a compatible substance index value for the first user with the biomarker result while a second user with the same biomarker for a urinary test of bacteria may be linked to a compatible substance index value for the second user. In an embodiment, compatible substance index value may contain different values for different biomarkers. For example, a compatible substance index value for yellow squash may have a high compatible substance index value for a user with a first genetic mutation but may have a low compatible substance index value for a user with a second genetic mutation or who does not contain the genetic mutation of the first user.

With continued reference to FIG. 13, compatible substance instruction set may contain at least a recommended compatible substance. Recommended compatible substance may include any food recommended for a user. In an embodiment, compatible substance instruction set may be filtered to contain foods that take into account user preference for eating particular foods or dietary eliminations due to food allergies or intolerances. This may be done for instance, such as by consulting user database 1200. In an embodiment, compatible substance instruction set may organize recommended compatible substances into categories such as for example utilizing the categorization scheme as described above in reference to FIG. 11 in compatible substance classification database 1100. For example, compatible substance instruction set may contain categories listing recommended compatible substances under each category such as for example a vegetable category that may include kale, cauliflower, and beets and a fruits and grain category that may contain watermelon, buckwheat, and couscous.

It is to be noted that any one or more of the aspects and embodiments described herein may be conveniently implemented using one or more machines (e.g., one or more computing devices that are utilized as a user computing device for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

Figure 14:
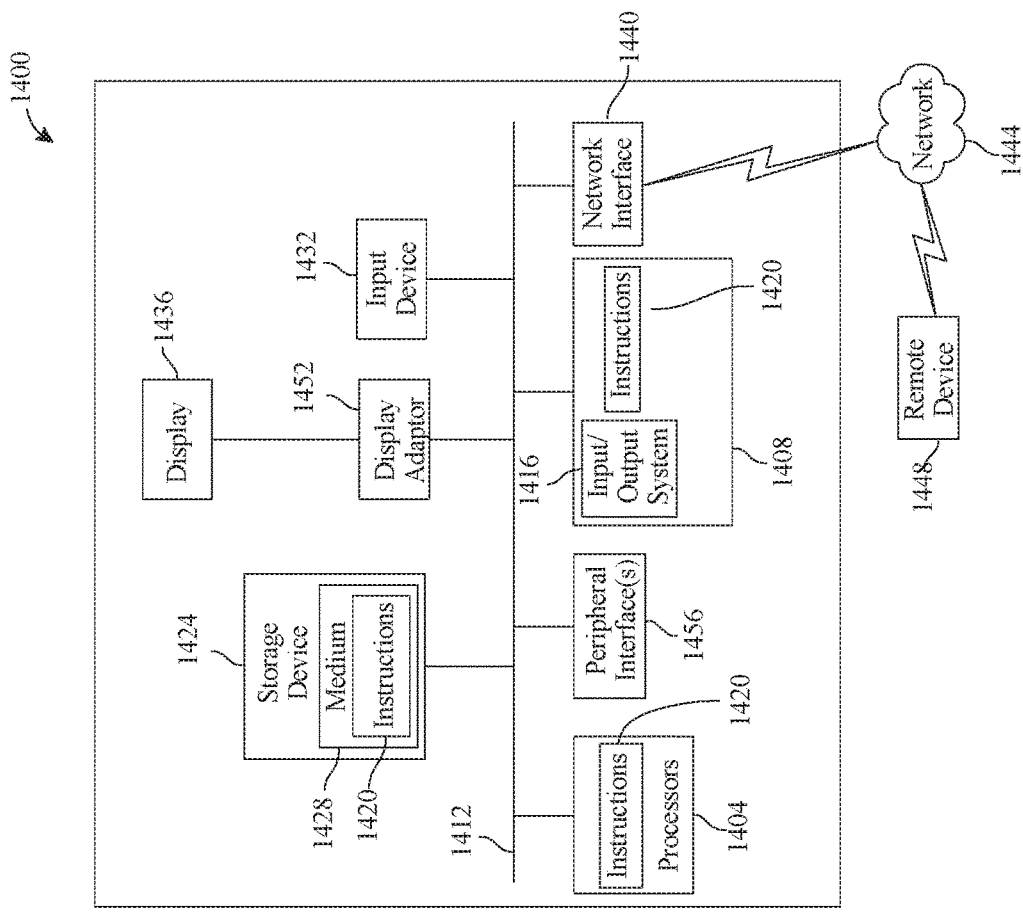
FIG. 14 is a block diagram of a computing system that can be used to implement any one or more of the methodologies disclosed herein and any one or more portions thereof.

FIG. 14 shows a diagrammatic representation of one embodiment of a computing device in the exemplary form of a computer system 1400 within which a set of instructions for causing a control system to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 1400 includes a processor 1404 and a memory 1408 that communicate with each other, and with other components, via a bus 1412. Bus 1412 may include any of several types of bus structures including, but not limited to, a memory bus, a memory controller, a peripheral bus, a local bus, and any combinations thereof, using any of a variety of bus architectures.

Memory 1408 may include various components (e.g., machine-readable media) including, but not limited to, a random access memory component, a read only component, and any combinations thereof. In one example, a basic input/output system 1416 (BIOS), including basic routines that help to transfer information between elements within computer system 1400, such as during start-up, may be stored in memory 1408. Memory 1408 may also include (e.g., stored on one or more machine-readable media) instructions (e.g., software) 1420 embodying any one or more of the aspects and/or methodologies of the present disclosure. In another example, memory 1408 may further include any number of program modules including, but not limited to, an operating system, one or more application programs, other program modules, program data, and any combinations thereof.

Computer system 1400 may also include a storage device 1424. Examples of a storage device (e.g., storage device 1424) include, but are not limited to, a hard disk drive, a magnetic disk drive, an optical disc drive in combination with an optical medium, a solid-state memory device, and any combinations thereof. Storage device 1424 may be connected to bus 1412 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 1424 (or one or more components thereof) may be removably interfaced with computer system 1400 (e.g., via an external port connector (not shown)). Particularly, storage device 1424 and an associated machine-readable medium 1428 may provide nonvolatile and/or volatile storage of machine-readable instructions, data structures, program modules, and/or other data for computer system 1400. In one example, software 1420 may reside, completely or partially, within machine-readable medium 1428. In another example, software 1420 may reside, completely or partially, within processor 1404.

Computer system 1400 may also include an input device 1432. In one example, a user of computer system 1400 may enter commands and/or other information into computer system 1400 via input device 1432. Examples of an input device 1432 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 1432 may be interfaced to bus 1412 via any of a variety of interfaces (not shown) including, but not limited to, a serial interface, a parallel interface, a game port, a USB interface, a FIREWIRE interface, a direct interface to bus 1412, and any combinations thereof. Input device 1432 may include a touch screen interface that may be a part of or separate from display 1436, discussed further below. Input device 1432 may be utilized as a user selection device for selecting one or more graphical representations in a graphical interface as described above.

A user may also input commands and/or other information to computer system 1400 via storage device 1424 (e.g., a removable disk drive, a flash drive, etc.) and/or network interface device 1440. A network interface device, such as network interface device 1440, may be utilized for connecting computer system 1400 to one or more of a variety of networks, such as network 1444, and one or more remote devices 1448 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 1444, may employ a wired and/or a wireless mode of communication. In general, any network topology may be used. Information (e.g., data, software 1420, etc.) may be communicated to and/or from computer system 1400 via network interface device 1440.

Computer system 1400 may further include a video display adapter 1452 for communicating a displayable image to a display device, such as display device 1436. Examples of a display device include, but are not limited to, a liquid crystal display (LCD), a cathode ray tube (CRT), a plasma display, a light emitting diode (LED) display, and any combinations thereof. Display adapter 1452 and display device 1436 may be utilized in combination with processor 1404 to provide graphical representations of aspects of the present disclosure. In addition to a display device, computer system 1400 may include one or more other peripheral output devices including, but not limited to, an audio speaker, a printer, and any combinations thereof. Such peripheral output devices may be connected to bus 1412 via a peripheral interface 1456. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve methods, systems, and software according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. A system for generating a compatible substance instruction set using artificial intelligence, the system comprising:
    at least a servers, wherein the at least a server is designed and configured to:
    receive a plurality of sets of training data, wherein each set of training data of the plurality of sets of training data correlating biomarker data to compatible substance labels;
    train a plurality of machine-learning models using the plurality of sets of training data, wherein:
        each machine-learning model of the plurality of machine-learning models further comprises a supervised machine-learning model; and
        training the plurality of machine-learning models further comprises training each machine-learning model with a set of training data of the plurality of sets of training data;
    store the plurality of machine-learning models in a machine-learning model database;
    receive at least a biomarker datum wherein the at least a biomarker datum contains at least an element of body data correlated to at least a body dimension;
    select a first training set, of the plurality of training sets using the at least a biomarker datum, wherein selecting the first training set further comprises:
        identifying, using an unsupervised machine-learning process, a correlation between a first element of biomarker data and a second element of biomarker data, wherein the second element of biomarker data is not included in any set of the plurality of training sets and the first element of biomarker data is included in the first training set;
        receiving the second element of biomarker data; and
        selecting the first element of biomarker data as a function of the second element of biomarker datum and the correlation;
    output, using a first machine-learning model, of the plurality of machine-learning models and trained using the first training set, and the at least a biomarker datum, a compatible substance label;
    determine a compatible substance index value using the compatible substance label and a compatible substance index value database; and
    generate at least a compatible substance instruction set containing the at least a compatible substance ranked as a function of the at least a compatible substance index value.

2. The system of claim 1, wherein receiving at least a biomarker datum further comprises receiving at least a tissue sample analysis correlated to at least a body dimension.

3. The system of claim 1, wherein receiving the plurality of training sets further comprises receiving at least an element of biomarker data from at least a constitutional analysis.

4. The system of claim 1, wherein receiving the plurality of training sets further comprises receiving at least an element of biomarker data from at least a tissue sample.

5. The system of claim 1, further configured to:
    retrieve the first machine-learning model from a database as a function of the first element of biomarker datum contained within the first training set.

6. The system of claim 1, further configured to wherein selecting at least a first machine-learning model further comprises:
    retrieve the first machine-learning model from a database as a function of the first element of biomarker datum contained within the first training set.

7. The system of claim 1, wherein generating at least a compatible substance instruction set further comprises:
    retrieving at least a compatible substance index value from a database; and
    generating at least a compatible substance instruction set as a function of the at least a compatible substance index value.

8. The system of claim 7, wherein generating at least a compatible substance instruction set further comprises evaluating the at least a compatible substance index value as a function of the at least a classified biomarker datum.

9. The system of claim 7, wherein generating at least a compatible substance instruction set further comprises:
    selecting at least a first compatible substance as a function of a first compatible substance index value; and
    selecting at least a second compatible substance as a function of the first compatible substance index value and a second compatible substance index value.

10. A method of generating a compatible substance instruction set using artificial intelligence, the method comprising:
    receiving, by at least a server, a plurality of sets of training data, wherein each set of training data of the plurality of sets of training data correlating biomarker data to compatible substance labels;
    training, by the at least a server, a plurality of machine-learning models using the plurality of sets of training data, wherein:
        each machine-learning model of the plurality of machine-learning models further comprises a supervised machine-learning model; and
        training the plurality of machine-learning models further comprises training each machine-learning model with a set of training data of the plurality of sets of training data;
    storing, by the at least a server, the plurality of machine-learning models in a machine-learning model database;
    receiving, by the at least a servers, at least a biomarker datum wherein the at least a biomarker datum contains at least an element of body data correlated to at least a body dimension;

selecting, by the at least a server, a first training set, of the plurality of training sets using the at least a biomarker datum, wherein selecting the first training set further comprises:
- identifying, using an unsupervised machine-learning process, a correlation between a first element of biomarker data and a second element of biomarker data, wherein the second element of biomarker data is not included in any set of the plurality of training sets and the first element of biomarker data is included in the first training set;
- receiving the second element of biomarker data; and
- selecting the first element of biomarker data as a function of the second element of biomarker datum and the correlation;

outputting, by the at least a server and using a first machine-learning model, of the plurality of machine-learning models and trained using the first training set, and the at least a biomarker datum, a compatible substance label;

determining, by the at least a server, a compatible substance index value using the compatible substance label and a compatible substance index value database; and generating by the at least a server at least a compatible substance instruction set containing the at least a compatible substance ranked as a function of the at least a compatible substance index value.

11. The method of claim 10, wherein receiving at least a biomarker datum further comprises receiving at least a tissue sample analysis correlated to at least a body dimension.

12. The method of claim 10, wherein receiving at least an element of data correlated to at least a body dimension further comprises at least a datum of user test data containing at least a root system label.

13. The method of claim 10, wherein receiving the plurality of training sets further comprises receiving at least an element of biomarker data from at least a constitutional analysis.

14. The method of claim 10, wherein receiving at least a first training set further comprises receiving at least a first element of classified biomarker data from at least a tissue sample.

15. The method of claim 10 further comprising:
retrieving the first machine-learning model from a database as a function of the first element of biomarker datum contained within the first training set.

16. The method of claim 10, wherein generating at least a compatible substance instruction set further comprises:
- retrieving at least a compatible substance index value from a database; and
- generating at least a compatible substance instruction set as a function of the at least a compatible substance index value.

17. The method of claim 16, wherein generating at least a compatible substance instruction set further comprises evaluating the at least a compatible substance index value as a function of the at least a classified biomarker datum.

18. The method of claim 16, wherein generating at least a compatible substance instruction set further comprises:
- selecting at least a first compatible substance as a function of a first compatible substance index value; and
- selecting at least a second compatible substance as a function of the first compatible substance index value and a second compatible substance index value.

* * * * *